United States Patent
Aerts

(12) 
(10) Patent No.: US 6,303,118 B1
(45) Date of Patent: Oct. 16, 2001

(54) HUMAN CHITINASE, ITS RECOMBINANT PRODUCTION, ITS USE FOR DECOMPOSING CHITIN, ITS USE IN THERAPY OR PROPHYLAXIS AGAINST INFECTION DISEASES

(75) Inventor: Johannes Maria Franciscus Gerardus Aerts, Abcoude (NL)

(73) Assignee: Universiteit Van Amsterdam, Amsterdm (NL)

( * ) Notice: Subject to any disclaimer, the term of this patent is extended or adjusted under 35 U.S.C. 154(b) by 0 days.

(21) Appl. No.: 09/343,623

(22) Filed: Jun. 30, 1999

Related U.S. Application Data

(62) Division of application No. 08/486,839, filed on Jun. 7, 1995, now Pat. No. 5,928,928.

(51) Int. Cl.[7] .............................. A61K 38/47; C12N 9/42; C12N 15/56
(52) U.S. Cl. ...................... 424/94.61; 435/209; 536/23.2
(58) Field of Search .................... 424/94.61; 435/209; 536/232

(56) References Cited

PUBLICATIONS

A.M. Pope et al. "The Influence of Carbohydrases on the Growth of Fungal Pathogens In vitro and In vivo", Medline Accession No. 80101245 citing Postgraduate Med. J. 55 (647): 674–646, Sep. 1979.*

D.A.L. Davies et al. "Mycolase, a New Kind of Systemic Antimycotic", Nature 273: 235–236, May, 1978.*

B. Overdijk et al., "Human Serun Contains a Chitinase: Identification of an Enzyme, Formerly Described as 4–Methylumbelliferyl–tetra–N–Acetylchitotetraoside Hydrolase (MU–Tact hydrolase)", Glycobiology 4(6): 797–803, 1994.*

Boot et al., The Journal of Biological Chemistry 270 (44): 26252–26256 (Nov. 1995).

Renkema et al., The Journal of Biological Chemistry 270 (5): 2198–2202 (Feb. 1995).

Hakala et al., The Journal of Biological Chemistry 268 (34): 25803–25810 (Dec. 1993).

Kramer et al., *Insect Biochemistry and Molecular Biology* 23(6): 691–701 (1993). Abstract only.

1988 Stratagene Catalog, p. 39 (1988).

* cited by examiner

Primary Examiner—Rebecca E. Prouty
(74) Attorney, Agent, or Firm—Hoffman & Baron, LLP

(57) ABSTRACT

A new human chitinase having an amino acid sequence as shown in FIG. 1 or FIG. 2. Modified forms of it having a similar chitin-hydrolyzing activity, and antigenic peptides representing one of its epitopes. Recombinant production of the human chitinase by genetically engineered hosts or host cells. Recombinant nucleic acid encoding it, and human chitinase-specific oligonucleotides. Use for therapeutic or prophylactic treatment of humans against infection by chitin-containing pathogens, or for decomposing chitin, e.g. from chitin-based articles. Antibodies binding to the human chitinase. Diagnostic test kits comprising the human chitinase, its antigenic peptides, human chitinase antibodies, recombinant nucleic acid or oligonucleotides.

6 Claims, 5 Drawing Sheets

FIG - 1

```
   1 CTG AGC TGC ATC ATG GTG CGG TCT GTG GCC TGG GCA GGT TTC ATG GTC CTG CTG    54
   1                 M   V   R   S   V   A   W   A   G   F   M   V   L   L      14

55 ATG ATC CCA TGG GGC TCT GCT GCA AAA CTG GTC TGC TAC TTC ACC AAC TGG GCC   108
  15  M   I   P   W   G   S   A   A   K   L   V   C   Y   F   T   N   W   A     32

109 CAG TAC AGA CAG GGG GAG GCT CGC TTC CTG CCC AAG GAC TTG GAC CCC AGC CTT   162
  33  Q   Y   R   Q   G   E   A   R   F   L   P   K   D   L   D   P   S   L     50

163 TGC ACC CAC CTC ATC TAC GCC TTC GCT GGC ATG ACC AAC CAC CAG CTG AGC ACC   216
  51  C   T   H   L   I   Y   A   F   A   G   M   T   N   H   Q   L   S   T     68

217 ACT GAG TGG AAT GAC GAG ACT CTC TAC CAG GAG TTC AAT GGC CTG AAG AAG ATG   270
  69  T   E   W   N   D   E   T   L   Y   Q   E   F   N   G   L   K   K   M     86

271 AAT CCC AAG CTG AAG ACC CTG TTA GCC ATC GGA GGC TGG AAT TTC GGC ACT CAG   324
  87  N   P   K   L   K   T   L   L   A   I   G   G   W   N   F   G   T   Q    104

325 AAG TTC ACA GAT ATG GTA GCC ACG GCC AAC AAC CGT CAG ACC TTT GTC AAC TCG   378
 105  K   F   T   D   M   V   A   T   A   N   N   R   Q   T   F   V   N   S    122

379 GCC ATC AGG TTT CTG CGC AAA TAC AGC TTT GAC GGC CTT GAC CTT GAC TGG GAG   432
 123  A   I   R   F   L   R   K   Y   S   F   D   G   L   D   L   D   W   E    140

433 TAC CCA GGA AGC CAG GGG AGC CCT GCC GTA GAC AAG GAG CGC TTC ACA ACC CTG   486
 141  Y   P   G   S   Q   G   S   P   A   V   D   K   E   R   F   T   T   L    158

487 GTA CAG GAC TTG GCC AAT GCC TTC CAG CAG GAA GCC CAG ACC TCA GGG AAC GAA   540
 159  V   Q   D   L   A   N   A   F   Q   Q   E   A   Q   T   S   G   K   E    176

541 CGC CTT CTT CTG AGT GCA GCG GTT CCA GCT GGG CAG ACC TAT GTG GAT GCT GGA   594
 177  R   L   L   L   S   A   A   V   P   A   G   Q   T   Y   V   D   A   G    194

595 TAC GAG GTG GAC AAA ATC GCC CAG AAC CTG GAT TTT GTC AAC CTT ATG GCC TAC   648
 195  Y   E   V   D   K   I   A   Q   N   L   D   F   V   N   L   M   A   Y    212

649 GAC TTC CAT GGC TCT TGG GAG AAG GTC ACG GGA CAT AAC AGC CCC CTC TAC AAG   702
 213  D   F   H   G   S   W   E   K   V   T   G   H   N   S   P   L   Y   K    230

703 AGG CAA GAA GAG AGT GGT GCA GCA GCC AGC CTC AAC GTG GAT GCT GCT GTG CAA   756
 231  R   Q   E   E   S   G   A   A   A   S   L   N   V   D   A   A   V   Q    248

757 CAG TGG CTG CAG AAG GGG ACC CCT GCC AGC AAG CTG ATC CTT GGC ATG CCT ACC   810
 249  Q   W   L   Q   K   G   T   P   A   S   K   L   I   L   G   M   P   T    266

811 TAC GGA CGC TCC TTC ACA CTG GCC TCC TCA TCA GAC ACC AGA GTG GGG GCC CCA   864
 267  Y   G   R   S   F   T   L   A   S   S   S   D   T   R   V   G   A   P    284

865 GCC ACA GGG TCT GGC ACT CCA GGC CCC TTC ACC AAG GAA GGA GGG ATG CTG GCC   918
 285  A   T   G   S   G   T   P   G   P   F   T   K   E   G   G   M   L   A    302

919 TAC TAT GAA GTC TGC TCC TGG AAG GGG GCC ACC AAA CAG AGA ATC CAG GAT CAG   972
 303  Y   Y   E   V   C   S   W   K   G   A   T   K   Q   R   I   Q   D   Q    320

973 AAG GTG CCC TAC ATC TTC CGG GAC AAC CAG TGG GTG GGC TTT GAT GAT GTG GAG  1026
 321  K   V   P   Y   I   F   R   D   N   Q   W   V   G   F   D   D   V   E    338

1027 AGC TTC AAA ACC AAG GTC AGC TAT CTG AAG CAG AAG GGA CTG GGC GGG GCC ATG  1080
 339  S   F   K   T   K   V   S   Y   L   K   Q   K   G   L   G   G   A   M    356

1081 GTC TGG GCA CTG GAC TTA GAT GAC TTT GCC GGC TTC TCC TGC AAC CAG GGC CGA  1134
 357  V   W   A   L   D   L   D   D   F   A   G   F   S   C   N   Q   G   R    374

1135 TAC CCC CTC ATC CAG ACG CTA CGG CAG GAA CTG AGT CTT CCA TAC TTG CCT TCA  1188
 375  Y   P   L   I   Q   T   L   R   Q   E   L   S   L   P   Y   L   P   S    392

1189 GGC ACC CCA GAG CTT GAA GTT CCA AAA CCA GGT CAG CCC TCT GAA CCT GAG CAT  1242
 393  G   T   P   E   L   E   V   P   K   P   G   Q   P   S   E   P   E   H    410

1243 GGC CCC AGC CCT GGA CAA GAC ACG TTC TGC CAG GGC AAA GCT GAT GGG CTC TAT  1296
 411  G   P   S   P   G   Q   D   T   F   C   Q   G   K   A   D   G   L   Y    428

1297 CCC AAT CCT CGG GAA CGG TCC AGC TTC TAC AGC TGT GCA GCG GGG CGG CTG TTC  1350
 429  P   N   P   R   E   R   S   S   F   Y   S   C   A   A   G   R   L   F    446

1351 CAG CAA AGC TGC CCG ACA GGC CTG GTG TTC AGC AAC TCC TGC AAA TGC TGC ACC  1404
 447  Q   Q   S   C   P   T   G   L   V   F   S   N   S   C   K   C   C   T    464

1405 TGG AAT TGA GTC GTA AAG CCC CTC CAG TCC AGC TTT GAG GCT GGG CCC AGG ATC  1458
 465  W   N   ***                                                              466

1459 ACT CTA CAG CCT GCC TCC TGG GTT TTC CTG GGG GCC GCA ATC TGG CTC CTG CAG  1512
1513 GCC TTT CTG TGG TCT TCC TTT ATC CAG GCT TTC TGC TCT CAG CCT TGC CTT CCT  1566
1567 TTT TTC TGG GTC TCC TGG GCT GCC CCT TTC ACT TGC AAA ATA AAT CTT TGG TTT  1620
1621 GTG CCC CTC TTC AAA AAA AAA AA
```

FIG - 2

```
   1 CTG AGC TGC ATC ATG GTG CGG TCT GTG GCC TGG GCA GGT TTC ATG GTC CTG CTG  54
   1                 M   V   R   S   V   A   W   A   G   F   M   V   L   L    14

55 ATG ATC CCA TGG GGC TCT GCT GCA AAA CTG GTC TGC TAC TTC ACC AAC TGG GCC 108
  15  M   I   P   W   G   S   A   A   K   L   V   C   Y   F   T   N   W   A   32

109 CAG TAC AGA CAG GGG GAG GCT CGC TTC CTG CCC AAG GAC TTG GAC CCC AGC CTT 162
  33  Q   Y   R   Q   G   E   A   R   F   L   P   K   D   L   D   P   S   L   50

163 TGC ACC CAC CTC ATC TAC GCC TTC GCT GGC ATG ACC AAC CAC CAG CTG AGC ACC 216
  51  C   T   H   L   I   Y   A   F   A   G   M   T   N   H   Q   L   S   T   68

217 ACT GAG TGG AAT GAC GAG ACT CTC TAC CAG GAG TTC AAT GGC CTG AAG AAG ATG 270
  69  T   E   W   N   D   E   T   L   Y   Q   E   F   N   G   L   K   K   M   86

271 AAT CCC AAG CTG AAG ACC CTG TTA GCC ATC GGA GGC TGG AAT TTC GGC ACT CAG 324
  87  N   P   K   L   K   T   L   L   A   I   G   G   W   N   F   G   T   Q  104

325 AAG TTC ACA GAT ATG GTA GCC ACG GCC AAC AAC CGT CAG ACC TTT GTC AAC TCG 378
 105  K   F   T   D   M   V   A   T   A   N   N   R   Q   T   F   V   N   S  122

379 GCC ATC AGG TTT CTG CGC AAA TAC AGC TTT GAC GGC CTT GAC CTT GAC TGG GAG 432
 123  A   I   R   F   L   R   K   Y   S   F   D   G   L   D   L   D   W   E  140

433 TAC CCA GGA AGC CAG GGG AGC CCT GCC GTA GAC AAG GAG CGC TTC ACA ACC CTG 486
 141  Y   P   G   S   Q   G   S   P   A   V   D   K   E   R   F   T   T   L  158

487 GTA CAG GAC TTG GCC AAT GCC TTC CAG CAG GAA GCC CAG ACC TCA GGG AAC GAA 540
 159  V   Q   D   L   A   N   A   F   Q   Q   E   A   Q   T   S   G   K   E  176

541 CGC CTT CTT CTG AGT GCA GCG GTT CCA GCT GGG CAG ACC TAT GTG GAT GCT GGA 594
 177  R   L   L   L   S   A   A   V   P   A   G   Q   T   Y   V   D   A   G  194

595 TAC GAG GTG GAC AAA ATC GCC CAG AAC CTG GAT TTT GTC AAC CTT ATG GCC TAC 648
 195  Y   E   V   D   K   I   A   Q   N   L   D   F   V   N   L   M   A   Y  212

649 GAC TTC CAT GGC TCT TGG GAG AAG GTC ACG GGA CAT AAC AGC CCC CTC TAC AAG 702
 213  D   F   H   G   S   W   E   K   V   T   G   H   N   S   P   L   Y   K  230

703 AGG CAA GAA GAG AGT GGT GCA GCA GCC AGC CTC AAC GTG GAT GCT GCT GTG CAA 756
 231  R   Q   E   E   S   G   A   A   A   S   L   N   V   D   A   A   V   Q  248

757 CAG TGG CTG CAG AAG GGG ACC CCT GCC AGC AAG CTG ATC CTT GGC ATG CCT ACC 810
 249  Q   W   L   Q   K   G   T   P   A   S   K   L   I   L   G   M   P   T  266

811 TAC GGA CGC TCC TTC ACA CTG GCC TCC TCA TCA GAC ACC AGA GTG GGG GCC CCA 864
 267  Y   G   R   S   F   T   L   A   S   S   S   D   T   R   V   G   A   P  284

865 GCC ACA GGG TCT GGC ACT CCA GGC CCC TTC ACC AAG GAA GGA GGG ATG CTG GCC 918
 285  A   T   G   S   G   T   P   G   P   F   T   K   E   G   G   M   L   A  302

919 TAC TAT GAA GTC TGC TCC TGG AAG GGG GCC ACC AAA CAG AGA ATC CAG GAT CAG 972
 303  Y   Y   E   V   C   S   W   K   G   A   T   K   Q   R   I   Q   D   Q  320

973 AAG GTG CCC TAC ATC TTC CGG GAC AAC CAG TGG GTG GGC TTT GAT GAT GTG GAG 1026
 321  K   V   P   Y   I   F   R   D   N   Q   W   V   G   F   D   D   V   E  338

1027 AGC TTC AAA ACC AAG GTC AGC TAT CTG AAG CAG AAG GGA CTG GGC GGG GCC ATG 1080
 339  S   F   K   T   K   V   S   Y   L   K   Q   K   G   L   G   G   A   M  356

1081 GTC TGG GCA CTG GAC TTA GAT GAC TTT GCC GGC TTC TCC TGC AAC CAG GGC CGA 1134
 357  V   W   A   L   D   L   D   D   F   A   G   F   S   C   N   Q   G   R  374

1135 TAC CCC CTC ATC CAG ACG CTA CGG CAG GAA CTG AAT GGG TAA AGC TTA AAC TGC 1188
 375  Y   P   L   I   Q   T   L   R   Q   E   L   N   G   ***                 388

1184 CTG TCA CAT GTG AGG CCA GGT GTT GCC TGT GGC ACT GTG CTT CAG CTG TAG GTC 1242
1243 TTC CAT ACT TGC CTT CAG GCA CCC CAG AGC TTG AAG TTC CAA AAC CAG GTC AGC 1296
1297 CCT CTG AAC CTG AGC ATG GCC CCA GCC CTG GAC AAG ACA CGT TCT GCC AGG GCA 1350
1351 AAG CTG ATG GGC TCT ATC CCA ATC CTC GGG AAC GGT CCA GCT TCT ACA GCT GTG 1404
1405 CAG CGG GGC GGC TGT TCC AGC AAA GCT GCC CGA CAG GCC TGG TGT TCA GCA ACT 1458
1459 CCT GCA AAT GCT GCA CCT GGA ATT GAG TCG TAA AGC CCC TCC AGT CCA GCT TTG 1512
1513 AGG CTG GGC CCA GGA TCA CTC TAC AGC CTG CCT CCT GGG TTT TCC TGG GGG CCG 1566
1567 CAA TCT GGC TCC TGC AGG CCT TTC TGT GGT CTT CCT TTA TCC AGG CTT TCT GCT 1620
1621 CTC AGC CTT GCC TTC CTT TTT TCT GGG TCT CCT GGG CTG CCC CTT TCA CTT GCA 1674
1675 AAA TAA ATC TTT GGT TTG TGC CCC TCA AAA AAA AAA AAA                      1713
```

FIG - 4

| | | | | | | | | | | |
|---|---|---|---|---|---|---|---|---|---|---|
|Chitotriosidase|F|D|G|L|D|L|D|W|E|Y|P|
|Chitinase Autographa californica|F|D|G|V|D|I|D|W|E|F|P|
|Chitinase Manduca sexta|F|D|G|L|D|L|D|W|E|Y|P|
|Chitinase Brugia malayi|F|D|G|F|D|L|D|W|E|Y|P|
|Oviductal glycoprotein Human|F|D|G|L|D|L|F|F|L|Y|P|
|Hcgp39 Human|F|D|G|L|D|L|A|W|L|Y|P|
|Ym1 Mouse|F|D|G|L|N|L|D|W|Q|Y|P|
|Chitinase Aphanocladium album|F|D|G|I|D|I|D|W|E|Y|P|
|Chitinase Trichoderma harzianum|F|D|G|I|D|V|D|W|E|Y|P|
|Chitinase A1 Bacillus circulans|F|D|G|V|D|L|D|W|E|Y|P|
|Chitinase Nicotiana tabacum class V|F|H|G|L|D|L|D|W|E|Y|P|

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: unknown
      (D) TOPOLOGY: unknown (ii) MOLECULE TYPE: other nucleic acid (iii) HYPOTHETICAL: NO (xi) SEQUENCE DESCRIPTION: SEQ ID NO: 1:

TGYTAYTTYA CNAAYTGGGC                                          20

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: unknown
      (D) TOPOLOGY: unknown (ii) MOLECULE TYPE: other nucleic acid (iii) HYPOTHETICAL: NO (ix) FEATURE:
      (A) NAME/KEY: misc_feature
      (B) LOCATION:6..15
      (D) OTHER INFORMATION:/product= "N represents inosine"

(xi) SEQUENCE DESCRIPTION: SEQ ID NO: 2:

CCARTCNARR TYNACNCCRT CRAA                                  24

(2) INFORMATION FOR SEQ ID NO: 3:

(i) SEQUENCE CHARACTERISTICS:
      (A) LENGTH: 1643 base pairs
      (B) TYPE: nucleic acid
      (C) STRANDEDNESS: unknown
      (D) TOPOLOGY: unknown (ii) MOLECULE TYPE: cDNA (iii) HYPOTHETICAL: NO (xi) SEQUENCE DESCRIPTION: SEQ ID NO: 3:

CTGAGCTGCA TCATGGTGCG GTCTGTGGCC TGGGCAGGTT TCATGGTCCT GCTGATGATC     60

CCATGGGGCT CTGCTCCAAA ACTGGTCTGC TACTTCACCA ACTGGGCCCA GTACAGACAG    120

```
GGGGAGGCTC GCTTCCTGCC CAAGGACTTG GACCCCAGCC TTTGCACCCA CCTCATCTAC    180

GCCTTCGCTG GCATGACCAA CCACCAGCTG AGCACCACTG AGTGGAATGA CGAGACTCTC    240

TACCAGGAGT TCAATGGCCT GAAGAAGATG AATCCCAAGC TGAAGACCCT GTTAGCCATC    300

GGAGGCTGGA ATTTCGGCAC TCAGAAGTTC ACAGATATGG TAGCCACGGC CAACAACCGT    360

CAGACCTTTG TCAACTCGGC CATCAGGTTT CTGCGCAAAT ACAGCTTTGA CGGCCTTGAC    420

CTTGACTGGG AGTACCCAGG AAGCCAGGGG AGCCCTGCCG TAGACAAGGA GCGCTTCACA    480

ACCCTGGTAC AGGACTTGGC CAATGCCTTC CAGCAGGAAG CCCAGACCTC AGGGAAGGAA    540

CGCCTTCTTC TGAGTGCAGC GGTTCCAGCT GGGCAGACCT ATGTGGATGC TGGATACGAG    600

GTGGACAAAA TCGCCCAGAA CCTGGATTTT GTCAACCTTA TGGCCTACGA CTTCCATGGC    660

TCTTGGGAGA AGGTCACGGG ACATAACAGC CCCCTCTACA AGAGGCAAGA AGAGAGTGGT    720

GCAGCAGCCA GCCTCAACGT GGATGCTGCT GTGCAACAGT GGCTGCAGAA GGGGACCCCT    780

GCCAGCAAGC TGATCCTTGG CATGCCTACC TACGGACGCT CCTTCACACT GGCCTCCTCA    840

TCAGACACCA GAGTGGGGGC CCCAGCCACA GGGTCTGGCA CTCCAGGCCC CTTCACCAAG    900

GAAGGAGGGA TGCTGGCCTA CTATGAAGTC TGCTCCTGGA AGGGGCCAC CAAACAGAGA    960

ATCCAGGATC AGAAGGTGCC CTACATCTTC CGGGACAACC AGTGGGTGGG CTTTGATGAT    1020

GTGGAGAGCT TCAAAACCAA GGTCAGCTAT CTGAAGCAGA AGGGACTGGG CGGGGCCATG    1080

GTCTGGGCAC TGGACTTAGA TGACTTTGCC GGCTTCTCCT GCAACCAGGG CCGATACCCC    1140

CTCATCCAGA CGCTACGGCA GGAACTGAGT CTTCCATACT TGCCTTCAGG CACCCCAGAG    1200

CTTGAAGTTC AAAACCAGG TCAGCCCTCT GAACCTGAGC ATGGCCCCAG CCCTGGACAA    1260

GACACGTTCT GCCAGGGCAA AGCTGATGGG CTCTATCCCA ATCCTCGGGA ACGGTCCAGC    1320

TTCTACAGCT GTGCAGCGGG GCGGCTGTTC AGCAAAGCT GCCCGACAGG CCTGGTGTTC    1380

AGCAACTCCT GCAAATGCTG CACCTGGAAT TGAGTCGTAA AGCCCCTCCA GTCCAGCTTT    1440

GAGGCTGGGC CCAGGATCAC TCTACAGCCT GCCTCCTGGG TTTTCCTGGG GGCCGCAATC    1500

TGGCTCCTGC AGGCCTTTCT GTGGTCTTCC TTTATCCAGG CTTTCTGCTC TCAGCCTTGC    1560

CTTCCTTTTT TCTGGGTCTC CTGGGCTGCC CCTTTCACTT GCAAAATAAA TCTTTGGTTT    1620

GTGCCCCTCT TCAAAAAAAA AAA                                           1643
```

(2) INFORMATION FOR SEQ ID NO: 4:

(i) SEQUENCE CHARACTERISTICS:
        (A) LENGTH: 466 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 4:

```
Met Val Arg Ser Val Ala Trp Ala Gly Phe Met Val Leu Leu Met Ile
1               5                   10                  15

Pro Trp Gly Ser Ala Ala Lys Leu Val Cys Tyr Phe Thr Asn Trp Ala
            20                  25                  30

Gln Tyr Arg Gln Gly Glu Ala Arg Phe Leu Pro Lys Asp Leu Asp Pro
        35                  40                  45

Ser Leu Cys Thr His Leu Ile Tyr Ala Phe Ala Gly Met Thr Asn His
    50                  55                  60
```

-continued

```
Gln Leu Ser Thr Thr Glu Trp Asn Asp Glu Thr Leu Tyr Gln Glu Phe
 65                  70                  75                  80

Asn Gly Leu Lys Lys Met Asn Pro Lys Leu Lys Thr Leu Leu Ala Ile
                 85                  90                  95

Gly Gly Trp Asn Phe Gly Thr Gln Lys Phe Thr Asp Met Val Ala Thr
            100                 105                 110

Ala Asn Asn Arg Gln Thr Phe Val Asn Ser Ala Ile Arg Phe Leu Arg
        115                 120                 125

Lys Tyr Ser Phe Asp Gly Leu Asp Leu Asp Trp Glu Tyr Pro Gly Ser
130                 135                 140

Gln Gly Ser Pro Ala Val Asp Lys Glu Arg Phe Thr Thr Leu Val Gln
145                 150                 155                 160

Asp Leu Ala Asn Ala Phe Gln Gln Glu Ala Gln Thr Ser Gly Lys Glu
                165                 170                 175

Arg Leu Leu Leu Ser Ala Ala Val Pro Ala Gly Gln Thr Tyr Val Asp
            180                 185                 190

Ala Gly Tyr Glu Val Asp Lys Ile Ala Gln Asn Leu Asp Phe Val Asn
        195                 200                 205

Leu Met Ala Tyr Asp Phe His Gly Ser Trp Glu Lys Val Thr Gly His
210                 215                 220

Asn Ser Pro Leu Tyr Lys Arg Gln Glu Glu Ser Gly Ala Ala Ala Ser
225                 230                 235                 240

Leu Asn Val Asp Ala Ala Val Gln Gln Trp Leu Gln Lys Gly Thr Pro
                245                 250                 255

Ala Ser Lys Leu Ile Leu Gly Met Pro Thr Tyr Gly Arg Ser Phe Thr
            260                 265                 270

Leu Ala Ser Ser Ser Asp Thr Arg Val Gly Ala Pro Ala Thr Gly Ser
        275                 280                 285

Gly Thr Pro Gly Pro Phe Thr Lys Glu Gly Gly Met Leu Ala Tyr Tyr
290                 295                 300

Glu Val Cys Ser Trp Lys Gly Ala Thr Lys Gln Arg Ile Gln Asp Gln
305                 310                 315                 320

Lys Val Pro Tyr Ile Phe Arg Asp Asn Gln Trp Val Gly Phe Asp Asp
                325                 330                 335

Val Glu Ser Phe Lys Thr Lys Val Ser Tyr Leu Lys Gln Lys Gly Leu
            340                 345                 350

Gly Gly Ala Met Val Trp Ala Leu Asp Leu Asp Asp Phe Ala Gly Phe
        355                 360                 365

Ser Cys Asn Gln Gly Arg Tyr Pro Leu Ile Gln Thr Leu Arg Gln Glu
370                 375                 380

Leu Ser Leu Pro Tyr Leu Pro Ser Gly Thr Pro Glu Leu Glu Val Pro
385                 390                 395                 400

Lys Pro Gly Gln Pro Ser Glu Pro Glu His Gly Pro Ser Pro Gly Gln
                405                 410                 415

Asp Thr Phe Cys Gln Gly Lys Ala Asp Gly Leu Tyr Pro Asn Pro Arg
            420                 425                 430

Glu Arg Ser Ser Phe Tyr Ser Cys Ala Ala Gly Arg Leu Phe Gln Gln
        435                 440                 445

Ser Cys Pro Thr Gly Leu Val Phe Ser Asn Ser Cys Lys Cys Cys Thr
450                 455                 460

Trp Asn
465
```

(2) INFORMATION FOR SEQ ID NO: 5:

(i) SEQUENCE CHARACTERISTICS:
        (A) LENGTH: 1713 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (xi) SEQUENCE DESCRIPTION: SEQ ID NO: 5:

```
CTGAGCTGCA TCATGGTGCG GTCTGTGGCC TGGGCAGGTT TCATGGTCCT GCTGATGATC      60
CCATGGGGCT CTGCTCCAAA ACTGGTCTGC TACTTCACCA ACTGGGCCCA GTACAGACAG     120
GGGGAGGCTC GCTTCCTGCC CAAGGACTTG GACCCCAGCC TTTGCACCCA CCTCATCTAC     180
GCCTTCGCTG GCATGACCAA CCACCAGCTG AGCACCACTG AGTGGAATGA CGAGACTCTC     240
TACCAGGAGT TCAATGGCCT GAAGAAGATG AATCCCAAGC TGAAGACCCT GTTAGCCATC     300
GGAGGCTGGA ATTTCGGCAC TCAGAAGTTC ACAGATATGG TAGCCACGGC CAACAACCGT     360
CAGACCTTTG TCAACTCGGC CATCAGGTTT CTGCGCAAAT ACAGCTTTGA CGGCCTTGAC     420
CTTGACTGGG AGTACCCAGG AAGCCAGGGG AGCCCTGCCG TAGACAAGGA GCGCTTCACA     480
ACCCTGGTAC AGGACTTGGC CAATGCCTTC CAGCAGGAAG CCCAGACCTC AGGGAAGGAA     540
CGCCTTCTTC TGAGTGCAGC GGTTCCAGCT GGGCAGACCT ATGTGGATGC TGGATACGAG     600
GTGGACAAAA TCGCCCAGAA CCTGGATTTT GTCAACCTTA TGGCCTACGA CTTCCATGGC     660
TCTTGGGAGA AGGTCACGGG ACATAACAGC CCCCTCTACA AGAGGCAAGA AGAGAGTGGT     720
GCAGCAGCCA GCCTCAACGT GGATGCTGCT GTGCAACAGT GGCTGCAGAA GGGGACCCCT     780
GCCAGCAAGC TGATCCTTGG CATGCCTACC TACGGACGCT CCTTCACACT GGCCTCCTCA     840
TCAGACACCA GAGTGGGGGC CCCAGCCACA GGGTCTGGCA CTCCAGGCCC CTTCACCAAG     900
GAAGGAGGGA TGCTGGCCTA CTATGAAGTC TGCTCCTGGA AGGGGCCAC CAAACAGAGA     960
ATCCAGGATC AGAAGGTGCC CTACATCTTC CGGGACAACC AGTGGGTGGG CTTTGATGAT    1020
GTGGAGAGCT TCAAAACCAA GGTCAGCTAT CTGAAGCAGA AGGGACTGGG CGGGGCCATG    1080
GTCTGGGCAC TGGACTTAGA TGACTTTGCC GGCTTCTCCT GCAACCAGGG CCGATACCCC    1140
CTCATCCAGA CGCTACGGCA GGAACTGAAT GGGTAAAGCC TTAACTGCCT GTCACATGTG    1200
AGGCCAGGTG TTGCCTGTGG CACTGTGCTT CAGCTGTAGG TCTTCCATAC TTGCCTTCAG    1260
GCACCCCAGA GCTTGAAGTT CCAAAACCAG GTCAGCCCTC TGAACCTGAG CATGGCCCAA    1320
GCCCTGGACA AGACACGTTC TGCCAGGGCA AAGCTGATGG GCTCTATCCC AATCCTCGGG    1380
AACGGTCCAG CTTCTACAGC TGTGCAGCGG GGCGGCTGTT CCAGCAAAGC TGCCCGACAG    1440
GCCTGGTGTT CAGCAACTCC TGCAAATGCT GCACCTGGAA TTGAGTCGTA AAGCCCCTCC    1500
AGTCCAGCTT TGAGGCTGGG CCCAGGATCA CTCTACAGCC TGCCTCCTGG GTTTTCCTGG    1560
GGGCCGCAAT CTGGCTCCTG CAGGCCTTTC TGTGGTCTTC CTTTATCCAG GCTTTCTGCT    1620
CTCAGCCTTG CCTTCCTTTT TTCTGGGTCT CCTGGGCTGC CCCTTTCACT TGCAAAATAA    1680
ATCTTTGGTT TGTGCCCCTC AAAAAAAAAA AAA                                 1713
```

(2) INFORMATION FOR SEQ ID NO: 6:

(i) SEQUENCE CHARACTERISTICS:
        (A) LENGTH: 387 amino acids
        (B) TYPE: amino acid (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 6:

Met Val Arg Ser Val Ala Trp Ala Gly Phe Met Val Leu Leu Met Ile
1               5                   10                  15

Pro Trp Gly Ser Ala Ala Lys Leu Val Cys Tyr Phe Thr Asn Trp Ala
                20                  25                  30

Gln Tyr Arg Gln Gly Glu Ala Arg Phe Leu Pro Lys Asp Leu Asp Pro
            35                  40                  45

Ser Leu Cys Thr His Leu Ile Tyr Ala Phe Ala Gly Met Thr Asn His
50                  55                  60

Gln Leu Ser Thr Thr Glu Trp Asn Asp Glu Thr Leu Tyr Gln Glu Phe
65                  70                  75                  80

Asn Gly Leu Lys Lys Met Asn Pro Lys Leu Lys Thr Leu Leu Ala Ile
                85                  90                  95

Gly Gly Trp Asn Phe Gly Thr Gln Lys Phe Thr Asp Met Val Ala Thr
                100                 105                 110

Ala Asn Asn Arg Gln Thr Phe Val Asn Ser Ala Ile Arg Phe Leu Arg
            115                 120                 125

Lys Tyr Ser Phe Asp Gly Leu Asp Leu Asp Trp Glu Tyr Pro Gly Ser
130                 135                 140

Gln Gly Ser Pro Ala Val Asp Lys Glu Arg Phe Thr Thr Leu Val Gln
145                 150                 155                 160

Asp Leu Ala Asn Ala Phe Gln Gln Glu Ala Gln Thr Ser Gly Lys Glu
                165                 170                 175

Arg Leu Leu Leu Ser Ala Ala Val Pro Ala Gly Gln Thr Tyr Val Asp
            180                 185                 190

Ala Gly Tyr Glu Val Asp Lys Ile Ala Gln Asn Leu Asp Phe Val Asn
            195                 200                 205

Leu Met Ala Tyr Asp Phe His Gly Ser Trp Glu Lys Val Thr Gly His
210                 215                 220

Asn Ser Pro Leu Tyr Lys Arg Gln Glu Glu Ser Gly Ala Ala Ala Ser
225                 230                 235                 240

Leu Asn Val Asp Ala Ala Val Gln Gln Trp Leu Gln Lys Gly Thr Pro
                245                 250                 255

Ala Ser Lys Leu Ile Leu Gly Met Pro Thr Tyr Gly Arg Ser Phe Thr
            260                 265                 270

Leu Ala Ser Ser Ser Asp Thr Arg Val Gly Ala Pro Ala Thr Gly Ser
            275                 280                 285

Gly Thr Pro Gly Pro Phe Thr Lys Glu Gly Gly Met Leu Ala Tyr Tyr
            290                 295                 300

Glu Val Cys Ser Trp Lys Gly Ala Thr Lys Gln Arg Ile Gln Asp Gln
305                 310                 315                 320

Lys Val Pro Tyr Ile Phe Arg Asp Asn Gln Trp Val Gly Phe Asp Asp
                325                 330                 335

Val Glu Ser Phe Lys Thr Lys Val Ser Tyr Leu Lys Lys Gly Leu
            340                 345                 350

Gly Gly Ala Met Val Trp Ala Leu Asp Leu Asp Asp Phe Ala Gly Phe
            355                 360                 365

Ser Cys Asn Gln Gly Arg Tyr Pro Leu Ile Gln Thr Leu Arg Gln Glu

```
            370             375             380
Leu Asn Gly
385

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 7:

Phe Asp Gly Leu Asp Leu Asp Trp Glu Tyr Pro
1               5                   10

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 8:

Phe Asp Gly Val Asp Ile Asp Trp Glu Phe Pro
1               5                   10

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 9:

Phe Asp Gly Phe Asp Leu Asp Trp Glu Tyr Pro
1               5                   10

(2) INFORMATION FOR SEQ ID NO: 10:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 10:

Phe Asp Gly Leu Asp Leu Phe Phe Leu Tyr Pro
1               5                   10

(2) INFORMATION FOR SEQ ID NO: 11:
```

(i) SEQUENCE CHARACTERISTICS:
    (A) LENGTH: 11 amino acids
    (B) TYPE: amino acid
    (C) STRANDEDNESS: unknown
    (D) TOPOLOGY: unknown (ii) MOLECULE TYPE: protein (iii) HYPOTHETICAL: NO (xi) SEQUENCE DESCRIPTION: SEQ ID NO: 11:

Phe Asp Gly Leu Asp Leu Ala Trp Leu Tyr Pro
1               5                   10

(2) INFORMATION FOR SEQ ID NO: 12:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 12:

Phe Asp Gly Leu Asn Leu Asp Trp Gln Tyr Pro
1               5                   10

(2) INFORMATION FOR SEQ ID NO: 13:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 13:

Phe Asp Gly Ile Asp Ile Asp Trp Glu Tyr Pro
1               5                   10

(2) INFORMATION FOR SEQ ID NO: 14:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 14:

Phe Asp Gly Ile Asp Val Asp Trp Glu Tyr Pro
1               5                   10

(2) INFORMATION FOR SEQ ID NO: 15:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown

```
            -continued (ii) MOLECULE TYPE: protein (iii) HYPOTHETICAL: NO (xi) SEQUENCE DESCRIPTION: SEQ ID NO: 15:

Phe Asp Gly Val Asp Leu Asp Trp Glu Tyr Pro
1               5                   10

(2) INFORMATION FOR SEQ ID NO: 16:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO: 16:

Phe His Gly Leu Asp Leu Asp Trp Glu Tyr Pro
1               5                   10
```

HUMAN CHITINASE, ITS RECOMBINANT PRODUCTION, ITS USE FOR DECOMPOSING CHITIN, ITS USE IN THERAPY OR PROPHYLAXIS AGAINST INFECTION DISEASES

This application is a divisional application of U.S. Ser. No. 08/486,839 filed on Jun. 7, 1995, issued as U.S. Pat. No. 5,928,928.

A human chitinase, its recombinant production, its use for decomposing chitin, its use in therapy or prophylaxis against infection diseases.

1. Field of the Invention

The subject invention is in the fields of therapeutical and prophylactic treatment of human individuals against infections, especially by chitin-containing organisms, and recombinant DNA technology for the production of a substance useful in the above treatment. The invention furthermore has implications on some other fields, such as diagnostics, gene therapy, controlled drug release from chitin-containing drug carriers or implants, and cosmetic, dental and even food products.

2. Background of the Invention

Infectious Diseases and Natural Defence

Man is constantly at risk for chronic infections by a variety of agents such as viruses, bacteria, fungi, protozoa and multicellular parasites. Some of the associated infectious diseases are seriously disabilitating or even life-threatening. In response to the threat exerted by these pathogens a variety of defence mechanisms, the so called immune responses, have evolved in mammalians. For an excellent overview on the topic see chapters 1, 2, 15 and 16 in ref.1.

A distinction can be made between innate (or non-adaptive) immune responses and adaptive immune responses. The latter type of response is highly specific for a particular pathogen and improves with each successive encounter with the infectious agent. The adaptive immune responses are mediated by various types of lymphocytes. The innate immune responses are primarily produced by the phagocytic cells. These more primitive responses are not based on a highly specific recognition and act as a first line of defence against infection. An important group of phagocytes are long-lived cells (monocyte/macrophages) that belong to the mononuclear phagocyte lineage. Monocytes are formed from bone marrow stem cells and enter the blood stream. These cells can migrate out into the tissue where they develop into various types of tissue macrophages. Examples are the microglial cells in brain, the alveolar macrophages in the lung, the Kupffer cells in the liver, the mesanglial phagocytes in the kidney, the splenic macrophages, the lymph node resident and recirculating macrophages and the synovial cells. The second category of phagocytes is formed by the polymorphonuclear neutrophils that are short-lived cells and constitute the majority of the blood leukocytes.

Role of Phagocytes in Defence

Well documented is the key role played by phagocytes in immunity to bacterial infections. Phagocytes are attracted chemotactically to a bacterial infection. Attachment to the bacterium can occur via numerous interactions, e.g. complement-mediated, antibody-mediated or mannose-binding protein-mediated or via lectin-oligosaccharide interaction. Subsequently, the organism is exposed to a sequence of killing mechanisms in phagosomes and lysosomes. Of great importance are the oxygen-dependent killing mechanisms that generate the superoxide anion and subsequently other reactive oxygen intermediates that are toxic. More recently the importance of killing via the nitric oxide pathway in neutrophils has become evident. Oxygen-independent killing is mediated by defensins, small cationic polypeptides, lysosomal enzymes, lysozyme and lactoferrin. The precise roles of phagocytes in immunity to fungal and parasite infections are less well understood, but it is thought that they are similar to those involved in resistance to bacterial infections.

Besides their direct role in killing of organisms, macrophages play other important roles in the immunity to foreign organisms. Firstly, these cells are very effective at presenting antigens to T lymphocytes followed by further responses of the immune system. Secondly, exposure of macrophages to microbial products can be accompanied by release of cytokines that affect other components of the immune system. Thirdly, macrophages respond to cytokines released by T lymphocytes. For example, in some parasite infections the body reduces damage by walling off the parasite behind a capsule of inflammatory cells. This T-lymphocyte dependent process results in local accumulation of macrophages that release fibrogenic factors which stimulate the formation of granulomatous tissue and ultimately fibrosis.

Intervention of Infectious Diseases

The natural defence mechanisms against pathogens are not always sufficiently effective to prevent clinical complications and (preventive) intervention is therefore required.

One preventive approach is immunization, i.e. stimulation of defence mechanisms by prior vaccination of the host with (components of) pathogens. To be effective, a vaccine must induce a long-lived response from the right kind of T-lympho-cytes that produce a strong cell-mediated immunity. Although vaccination has proved to be effective for some pathogens, a number of intrinsic problems are associated with this approach. Most importantly, it has to be avoided that antigens used for vaccination induce the wrong kind of immune response, such as suppression or even autoimmunity. With some infections there is a need to achieve immunity in specific body locations that can be only obtained by local or oral immunization. Due to the complexity of the immune system, the heterogeneity in pathogens and the ability of some pathogens to escape from the specific immune responses, a generalized approach for effective immunization against pathogens is not available. Various strategies for specific infectious diseases remain under investigation by trial and error.

Another approach in the intervention of infectious diseases is the use of pharmacological agents that prevent further proliferation or survival of pathogens. In this connection use is made preferably of compounds that specifically act at the level of the pathogen and do not affect the host. Such specificity is based on differences in the composition and needs of mammalian cells and their pathogenic invaders. Some illustrative examples are the following. Penicillins and cephalosporins are specific inhibitors of bacterial cell wall synthesis. Aminoglycosides, chloramphenicol, tetracyclines, macrolides are inhibitors of bacterial protein synthesis; rifampicin, 4-quinolones are specific inhibitors of bacterial DNA replication. Amphotericin B and nystatin are antibiotics that are fungicidal due to binding specific sterols in the fungal cell membrane, thus causing leakage of cell components.

The pharmacological approach to intervene with pathogens at the level of a specific target that is absent in the host cells is also used in nature. A good example is the hydrolase lysozyme that is present in vertebrates as well as many invertebrates. Cell walls of many bacteria contain interlinked polymers of muramic acid and N-acetylglucosamine. The hydrolase lysozyme is capable of cleaving the glucosidic bond between muramic acid and N-acetylglucosamine moieties and consequently the integrity of the cell wall. The presence of lysozyme is without harm for the host since a similar structure is absent in non-bacterial cells.

Chitin

Chitin is a glycopolymer that is absent in mammalian cells but is present in a variety of organisms that cause infectious diseases in man. Chitin therefore forms an attractive target for selectively attacking these type of pathogens.

Chitin is a polymer of $\beta(1-4)$ linked N-acetyl-D-glucosamine units. It may also contain glucosamine units in different proportions. Mainly deacetylated chitin is called chitosan. For overviews on the topic see refs.2–5.

Chitin and its derivatives are one of the most abundant macromolecular biological products on earth. The estimated annual production is 10,000–100,000 million tons. Chitin is a structural component of cell walls of fungi and of the exoskeleton of almost all invertebrates (except sponges, most anthozoa, scyphozoa, and echinoderms), but is absent in vertebrates and autotrophic organisms. Chitin fulfils important functions: it protects cells and organisms against mechanical and chemical stress from the environment and it also supports and determines their shape. The chain length of N-acetylglucosamine polymers may differ from 100 to 8000 units. The polymers assemble laterally to form microfibrils, stabilized by strong hydrogen bonds between the amine group of sugar in one chain and the carbonyl group of sugar in a neighbouring chain. Three crystallographic forms of chitin can be recognized. In a-chitin, the most abundant form in fungi and arthropods, adjacent chains are oriented antiparallel. In $\beta$-chitin the chains are oriented parallel, whilst in $\gamma$-chitin two chains are parallel and the third one anti-parallel. The microfibrils in crustacea and fungi usually show a diameter of 20–25 nm. In most structures, chitin is associated with other substances. In fungal cell walls the accompanying compound is $\beta$-glucan. In exoskeletons of animals, chitin protein associations are however predominant. The matrix is hardened by deposition of calcium carbonate and phosphate as in crustacea or by tanning with phenolic derivatives as in insects. In chitinous structures of protozoa also glycoproteins and mucopolysaccharides are present.

Chitin and related compounds have found many applications. Chitosan is used as component of threads, fibers, films and gels. In the agricultural industry, seeds can be protected from fungi using a capsule containing chitin derivatives. In the food industry, chitosan is used in the preparation of fruit juices and soluble coffee. The cosmetic industry produces shampoos, gels, creams and even sponges containing chitosan. In the pharmaceutical industry and in medicine, chitosan occurs in the making of contact lenses, of drug excipients and of dressings for burns.

Chitin Synthesis and Degradation by Chitinases

The synthesis of chitin is the best understood for fungi. The essential precursor is UDP-N-acetylglucosamine that is synthesized from glucose. Chitin synthetases are transported as transmembrane proteins to the plasma membrane where they add N-acetylglucosamine from the donor UDP-N-acetylglucosamine across the membrane to the growing polysaccharide chain. Fungal synthetase can be competitively inhibited by polyoxins (produced by Streptomyces cacaoi) and nikkomycins (produced by Strepto-myces tentae), both being analogues of UDP-N-acetylglucosamine.

Chitin synthesis in other species is less well documented. It is suggested that in insects and crustacea chitin synthesis begins in the endoplasmic reticulum via glycosylation of a protein to which a chitin chain is added in the Golgi apparatus. The chitoprotein is subsequently exported to the cell surface. Chitin synthesis in arthropods appears to be a two-step process involving lipid-linked intermediates. The synthesis in arthropods can be specifically inhibited by insecticides of the benzoylphenylurea type of which the mechanism of action is still not precisely known. Furthermore inhibitors of protein synthesis and N-linked glycosylation (tunicamycin) inhibit the synthesis of chitin in these organisms. Evidence so far suggests that chitin synthesis in protozoa occurs at the cell surface and most likely resembles the process in fungi.

All chitin-containing organisms presumably contain enzyme systems that allow them to degrade the chitin polymer in order to allow morphogenesis, i.e. essential modifications of their shape. Furthermore, many higher plants, fish and insectivorous animals (including vertebrates) are capable of producing enzymes that can degrade chitin. Several enzymatic systems are in this respect distinguishable: i) $\gamma$-hexosaminidases are capable of removing the terminal N-acetylglucosamine moiety from the non-reducing end of the polysaccharide; ii) some lysozymes with a broad specificity (e.g. egg white lysozyme) are capable to cleave also within the chitin glycopolymer; iii) so called exochitinases cleave diacetylchiobiose units from the non-reducing end of the polysaccharide; and iv) specific endochitinases cleave glycosidic linkages randomly along the chitin chain, eventually giving diacetylchitobiose as major product, together with some triacetylchitotriose. The exo- and endochitinases are often exclusively named chitinases. This nomenclature is also used herein.

Chitinases are widespread in nature and have been found in some viruses, bacteria, fungi, plants, invertebrates and vertebrates. Chitinases constitute families 18 and 19 of glycosylhydrolases. This classification proposed by Henrissat is based on amino acid sequence similarity (6). Family 19 only contains plant chitinases; for example, the chitinase from Hordeum vulgare for which the 3-dimensional structure has been resolved. Only the so called class III plant chitinases belong to the family 18 of glycosylhydrolases. There is a considerable homology in the putative active site regions in chitinases of the family 18 of glycosylhydrolases. The proposed structure for the catalytic domain is a 8-stranded $\alpha/\beta$ barrel ('TIM barrel') (7,8). The reaction mechanism seems to be similar to that of lysozyme and most other glycosyhydrolases, i.e. general acid-base catalysis (8).

Infectious Diseases in Man Caused by Pathogens Containing Chitin

A variety of infectious diseases in man are caused by organisms that contain chitin. The most prominent ones are listed in Table 1. On the basis of the type of pathogen a classification can be made in: i) fungal infections; ii) protozoal infections; and iii) helminth (worm) infections. For an overview on the topic see for example ref.9.

Table 1

Some infectious diseases caused by chitin-containing pathogens

I. Fungal infections
   Cutaneous mycoces
   Subcutaneous mycoces
   Pulmonary mycoces
   Candidiasis
II. Protozoal infections
   Toxoplasmosis
   Malaria (Plasmodium species)
   Leishmaniasis (Leishmania species)
   Chagas disease, sleeping sickness (Trypanosoma species)
III. Helminth infections
   Schistosomiasis
   Trichinosis
   Filariasis
   Ochocerciasis Fungal Infections The limited number of presently available anti-fungal drugs are in general not very potent. Fungal infections are regularly encountered in immuno-incompetent people, currently most frequently in patients with acquired immunodeficiency syndrome (AIDS). Most fungal infections of the skin are treated with topical preparations. Visceral infections and cuticular infections require prolonged systemic therapy.

The most frequent fungal infection is caused by Candida albicans. The organism is a common commensal of the oral and vaginal mucosae but can become a pathogen on damaged skin, in severely ill patients, in patients who have specific immune deficiency, and in patients receiving broad-spectrum antibiotics when the local microbial ecology is disturbed. Extreme consequences of Candida infection can be pneumonia, endocarditis, septicaemia and even death. The only effective treatment is intravenous administration of amphotericin B. Administration of this drug can result in serious adverse affects that are accompanied by hypotension and collapse. For that reason an initial test dose is infused to determine the tolerance. Flucytosine is a synthetic fluorinated pyrimidine which enters fungal cells and inhibits metabolism by interfering with DNA and RNA synthesis. The compound is usually given in combination with amphotericin B for treatment of systemic fungal infections. When administered alone, resistance towards flucytosine rapidly develops.

Other species of fungi that can cause severe infectious diseases in man are Aspergillus, Cryptococcus, Coccidioides, Paracoccidioides, Blastomyces, Sporothrix, and Histoplasma capsulatum.

The clinical features of the more commonly encountered histoplasmosis may differ considerably. Histoplasma capsulatum infects macrophages and the pathogenesis of the disease is in some aspects similar to that of tuberculosis. In normal hosts acute pulmonary infection is often accompanied by cough and chest pain, myalgia and weight loss. In individuals with structural defects of the lung a chronic destructive disease in the lung apices may develop, similar to tuberculosis. In immunocompromised hosts disseminated histoplasmosis may develop, accompanied by fever, hepatosplenomegaly, anaemia, leucopenia, thrombocytopenia and pneumonia. Amphotericin B is the common choice of treatment. In view of its toxicity, treatment of various fungal infections with other drugs is investigated.

Protozoal and Helminth Infections

Protozoa are single-cell organisms that are causing a large number of severe infectious diseases in man (see Table 1). Fortunately for most of these pathogens effective treatment with drugs is feasible. The treatment of Chagas disease, caused by Trypanosoma cruzi, is at present not satisfactory. The heart and the gut are the organs severely affected in the chronic form of this disease. Effective treatment of tissue cysts of Toxoplasma gondii is not feasible. Reactivation of the disease may occur following depression of cell-mediated immunity. Helminth infections can be generally quite effectively cured with specific drugs. A major health problem in this respect is formed by lymphatic filariasis caused by Wucheria bancrofti and Brugia species. In an advanced state of the disease killing of microfilariae by the drug diethylcarbamzine (DEC) may result in complications as the result of responses to death of massive amounts of worms.

Improved Resistance Against Chitin-containing Pathogens by Interaction at the Level of Chitin The differential distribution of chitin among organisms has lead to the idea that chitin metabolism is an attractive target for controlling infections by chitin-containing organisms. Two distinct experimental approaches should be mentioned.

1. Chitin synthesis inhibition (for a review see ref.2)

The value of inhibitors of fungal cell wall synthesis as fungicides has been largely investigated in plants. Polyoxins have been widely used as excellent agricultural fungicides. The polyoxins are a group of related competitive inhibitors of the chitin synthetase reaction due to their structural resemblance to UDP-N-acetylglucosamine. More recently, nikkomycin has been detected as a potent inhibitor with a similar mechanism of action.

Benzoylaryl ureas are commercial insecticides which are highly potent inhibitors of chitin synthesis in insects but not in fungi.

Medical applications in man of the above compounds have not been documented.

2. Chitinases as vaccine

The importance of chitinase activity in the life cycle of protozoa has stimulated several investigators to consider the protist chitinases an attractive antigen for vaccination (10–13). Moreover, because it is so far (incorrectly) assumed that analogous proteins are not present in man (see e.g. ref.13).

The experimental approaches described above may be less advantageous in the battle against chitin-containing organisms than assumed.

Firstly, inhibition of chitin synthesis by synthetic compounds may be less specific and effective than hoped for. It cannot be excluded that inhibitors also interfere with endogenous processes in mammalian cells and consequently result in side-effects. Toxicity could also arise as a result of biotransformation of the original compound to a toxic product. Furthermore, prolonged administration of large quantities of drugs may be required due to the fact that these compounds are excreted via the urine. Moreover, alternative synthesis routes of chitin may exist or develop in organisms, complicating its complete inhibition.

Secondly, the use of chitinases from pathogenic organisms as a vaccine may result in unforeseen harmful side-effects. It cannot be excluded that fragments of such chitinases share homology with endogenous proteins and that an undesired immune response is elicited. This may in fact be more than a theoretical problem because of the strong homology between human chitinase and chitinases from other species (see below).

Role of Chitinases in Plants and Fish in Resistance Against Chitin-containing Pathogens Many plant chitinases are considered pathogenesis-related (PR) proteins. The enzymes are induced by the presence of (extracts of) pathogens, or other forms of stress. For some of the plant chitinases an anti-fungal role has been documented in vitro. For an overview see ref.14. Most strikingly, it was reported that spraying plants with a bacterial chitinase (ChiA) from Serratia marcescens expressed in E. coli renders protection against fungi (15). It is clear however that more effective inhibition of most fungi requires the concomitant presence of chitinase and β-1,3-glucanases. In plants, the latter enzymes are also induced in response to stress.

It has been reported that leucocytes of fish are rich in chitinase activity and fulfil a role in defence (16). Evidence for such a role was recently provided by the demonstration of an inhibitory action of purified chitinase fom turbot against the chitinous fungus Mucor mucedo.

At present it is generally believed that man does not contain a comparable chitinase in phagocytes. However, as will be discussed in detail below, we noted recently the presence of a similar type of enzyme in cultured human macrophages.

SUMMARY OF THE INVENTION

Given the limitations of current approaches to tackle chitin-containing pathogens, a novel approach is here proposed to solve the problem that constitutes a major threat to the welfare of man. The approach is based on the use of a recently identified human chitinase, which can be produced by recombinant DNA technology (biotechnology), as a safe and effective agent against chitin-containing pathogens, i.e. for intervention of infectious diseases caused by chitin-containing pathogens. The conception of the approach and its further development is described below.

The subject invention provides a substantially isolated or purified chitinase, said chitinase being a human chitinase having an amino acid sequence essentially corresponding to the amino acid sequence shown in FIG. 1 (SEQ ID NO:4) or the amino acid sequence shown in FIG. 2 (SEQ ID NO:6), or being a modified form of said human chitinase having a substantially similar chitin-hydrolyzing activity. It is preferred that this new human chitinase is produced by a genetically engineered host cell and isolated from said host cell or medium in which said host cell is cultured, wherein the amino acid sequence of the enzyme is encoded by a nucleotide sequence essentially corresponding to the nucleotide sequence shown in FIG. 1 (SEQ ID NO:3) or the nucleotide sequence shown in FIG. 2 (SEQ ID NO:5). The subject invention particularly includes a chitinase having an amino acid sequence essentially corresponding to the amino acid sequence shown in FIG. 1 (SEQ ID NO:4) and having a molecular weight of about 50 kDa, and a chitinase having an amino acid sequence essentially corresponding to the amino acid sequence shown in FIG. 2 (SEQ ID NO:6) and having a molecular weight of about 39 kDa.

The phrase "substantially isolated or purified" indicates that the chitinase is removed from an environment in which it naturally occurs, or from an environment in which it is produced or secreted as a result of the application of recombinant DNA technology, or as a result of chemical synthesis. It is intended that the invention embraces the chitinase in a "substantially isolated" form in which it is substantially separated or freed from other components of said environment, and it is preferred that the chitinase is "substantially purified", which means that it is sufficiently purified to be useful for pharmaceutical use, i.e. is pharmaceutically acceptable.

Although the invention covers the possibility of isolating the chitinase from a natural source of it, such as properly activated human macrophages, its production by recombinant DNA techniques or by chemical synthesis are preferred, especially its production by a genetically engineered host or host cell and isolation from said host or host cell or from medium in which said host cell is cultured.

The phrase "essentially corresponding to" intends to allow for small sequence variations, such as the naturally occurring variations which do not significantly affect the activity of the enzyme. Some amino acids of the human chitinase sequence may be replaced by others, or be deleted, without thereby significantly affecting the function, activity and tolerability of the enzyme, and may sometimes even improve one characteristic or the overall properties of the enzyme. Generally, such sequence variations will be quite limited, say to about less than 30%, more often less than 20% or even less than 10% of all amino acids, i.e. the variants will generally have a high homology of above 70%, more often above 80% or even above 90%, compared to the sequences shown in FIGS. 1 and 2 (SEQ ID NO:4 and 6). All have in common the functional characteristic of chitinase activity, which can be measured for typical chitinase substrates, such as 4-methylumbelliferyl-chitotrioside.

The phrase "a modified form of said human chitinase having a substantially similar chitin-hydrolyzing activity" intends to embrace variants whose amino acid sequence differs significantly from the sequences shown in FIGS. 1 and 2 (SEQ ID NO:4 and 6) but which yet have a similar chitinase activity. Such modified forms having similar or even improved properties could be designed on the basis of the module or domain structure of the human chitinase, such as constructs lacking a domain which is not required or even disadvantageous for activity, and constructs containing two or more copies of a domain whose amplified presence is desirable.

The phrase "having a substantially similar chitin-hydrolyzing activity" intends to set the minimum requirement of having an at least equivalent chitinase activity compared to the human chitinases shown in FIGS. 1 and 2 (SEQ ID NO:3–6). "Equivalent" refers to equivalency in substrate range, i.e. qualitatively, and to equivalency in activity value, i.e. quantitatively.

The subject invention furthermore provides a pharmaceutical composition comprising the new human chitinase as defined herein and a pharmaceutically acceptable carrier or diluent, more in particular a pharmaceutical composition for therapeutic or prophylactic treatment of a human individual against infection by a chitin-containing pathogen, comprising a therapeutically or prophylactically effective amount of the new human chitinase and a pharmaceutically acceptable carrier or diluent. Preferably the pharmaceutical composition further comprises a therapeutically or prophylactically effective amount of a human β-1,3-glucanase.

The invention also provides non-pharmaceutical compositions comprising the new human chitinase and a carrier or diluent. For example, such composition may be a medium for culturing cells, in particular human cells, or be a cosmetic (e.g. body lotion), dental (e.g. tooth paste, mouth rinse) or food product (e.g. milk, cheese and other dairy products).

Furthermore, this invention provides chitin-based articles of manufacture comprising a chitin-hydrolyzing amount of the new human chitinase. E.g., the chitin-based article of manufacture may be a drug-containing drug carrier or implant for controlled drug release, or a transient functional implant.

This invention also provides a method of therapeutic or prophylactic treatment of a human individual against infection by a chitin-containing pathogen, comprising administering to said human individual a pharmaceutical composition comprising a therapeutically or prophylactically effective amount of the new human chitinase.

The subject invention also provides a process for preparing a human chitinase having an amino acid sequence essentially corresponding to the amino acid sequence shown in FIG. 1 (SEQ ID NO:4) or the amino acid sequence shown in FIG. 2 (SEQ ID NO:6), or a modified form of said human chitinase having a substantially similar chitin-hydrolyzing activity, comprising growing a genetically engineered host or host cell capable of producing said human chitinase or modified form thereof and isolating the chitinase produced from said host or host cell or from medium in which said host cell is cultured. In this process, preferably the amino acid sequence of said chitinase is encoded by a nucleotide sequence essentially corresponding to the nucleotide sequence shown in FIG. 1 (SEQ ID NO:3) or the nucleotide sequence shown in FIG. 2 (SEQ ID NO:5).

The invention also provides a genetically engineered host cell capable of producing a human chitinase having an amino acid sequence essentially corresponding to the amino acid sequence shown in FIG. 1 (SEQ ID NO:4) or the amino acid sequence shown in FIG. 2 (SEQ ID NO:6), or a modified form of said human chitinase having a substantially similar chitin-hydrolyzing activity.

This invention also provides a recombinant nucleic acid comprising a nucleotide sequence encoding, or complementary to a nucleotide sequence encoding, an amino acid sequence essentially corresponding to the amino acid sequence shown in FIG. 1 (SEQ ID NO:4) or the amino acid sequence shown in FIG. 2 (SEQ ID NO:6). Preferably, said nucleotide sequence essentially corresponds to, or essentially is complementary to, the nucleotide sequence shown in FIG. 1 (SEQ ID NO:3) or the nucleotide sequence shown in FIG. 2 (SEQ ID NO:5).

The phrase "essentially complementary to" intends to cover all variants which can bind by hybridisation to the nucleotide sequences shown in FIGS. 1 and 2 (SEQ ID NOS:3 and 5), especially under stringent hybridisation conditions. The phrase "essentially corresponds to" intends to embrace all variants coding for the same or an equivalent (as to chitinase activity) amino acid sequence and being expressible by a host or host cell.

The invention also embraces oligonucleotides of at least about 8 nucleotides having a nucleotide sequence corresponding to, or complementary to, a nucleotide sequence shown in FIG. 1 (SEQ ID NO:3) or a nucleotide sequence shown in FIG. 2 (SEQ ID NO:5) and being capable of binding by hybridisation under stringent (i.e. requiring about complete complementarity) hybridisation conditions to a nucleic acid coding for the new human chitinase. Such oligonucleotides can be useful for different purposes, e.g. as a primer for use in nucleic acid amplification methods such as PCR, NASBA etc., or as a probe in hybridisation analysis. The length will usually depend on the intended use. When used as a primer, the length will normally be between 12, preferably 15, and 25, preferably 20 nucleotides. When used as a probe, the length will usually be somewhat higher, e.g. from about 15 or 20 up to about 40 or 50 nucleotides, or even up to the complete length of the coding sequence.

Similarly, this invention furthermore embraces peptides of at least about 8 amino acid residues having an amino acid sequence derived from the amino acid sequence shown in FIG. 1 (SEQ ID NO:4) or the amino acid sequence shown in FIG. 2 (SEQ ID NO:6) and representing or mimicking an epitope of the new human chitinase, in particular those having an amino acid sequence corresponding to an amino acid sequence shown in FIG. 1 (SEQ ID NO:4) or an amino acid sequence shown in FIG. 2 (SEQ ID NO:6) and having antigenicity. Usually, such peptides will have a length of at least about 10, or even at least about 15 amino acid residues, and up to about 40, preferably up to about 30 amino acid residues. Said peptides can be used for diagnostic purposes, or in immunization protocols to raise human chitinase-specific antibodies.

The invention also embraces antibodies capable of binding to the new human chitinase, especially monoclonal antibodies. Such antibodies can be used for many purposes, for example for isolating and/or purifying (e.g. by affinity chromatography) the human chitinase, or for diagnostic purposes.

The subject invention furthermore provides a diagnostic kit comprising such a human chitinase-binding antibody, or a human chitinase peptide as defined above, or the new human chitinase itself as defined herein, together with a conventional component of diagnostic kits for detecting an antigen or an antibody; and a diagnostic kit comprising a human chitinase-specific oligo-nucleotide or recombinant human chitinase-encoding nucleic acid as defined herein, together with a conventional component of diagnostic kits for detecting a nucleic acid.

Furthermore, the subject invention provides a method of decomposing chitin comprising contacting said chitin with the new human chitinase under chitin-hydrolyzing conditions.

BRIEF DESCRIPTION OF THE DRAWINGS

FIG. 1. Nucleotide sequence of chi.50 cDNA clone (SEQ ID NO:3) and predicted amino acid sequence of corresponding protein (SEQ ID NO:4).

FIG. 2. Nucleotide sequence of chi.39 cDNA clone (SEQ ID NO:5) and predicted amino acid sequence of corresponding protein.

FIG. 4. Alignment of putative active site regions in some members of the chitinase protein family (SEQ ID NO:7–16).

DETAILED DESCRIPTION OF THE INVENTION

Figure 3:
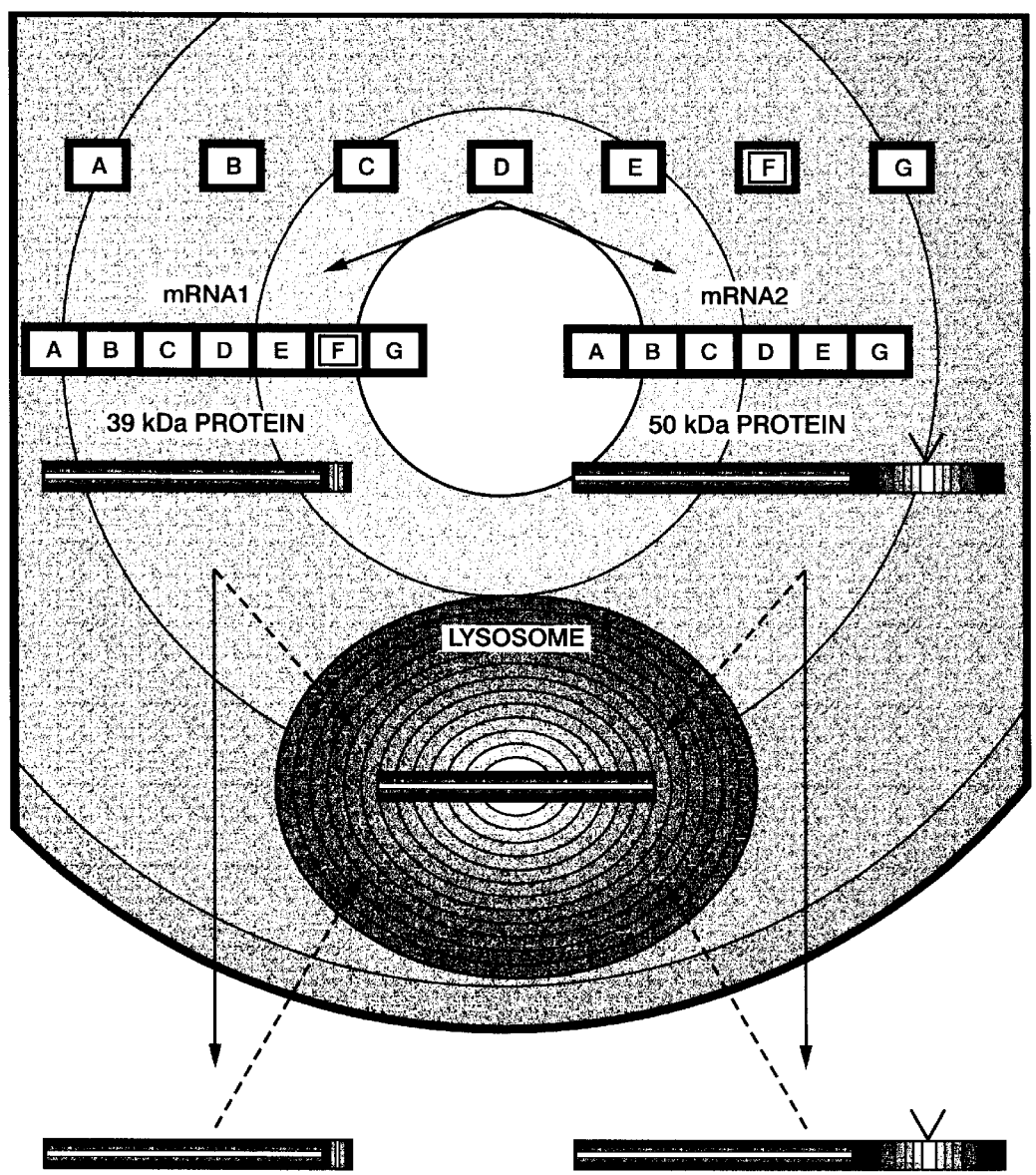
FIG. 3. Schematic overview of various chitotriosidase isozymes produced in macrophages.

The fact that man is continuously exposed to chitin (or chitin-containing organisms) strongly suggests that man should also have the ability to degrade this material. A gradual, presumably lysosomal, accumulation of chitin would otherwise inevitably occur in life, e.g. in alveolar macrophages that are in continuous contact with chitin-containing organisms. However, such storage of chitin has never been noted. This prompted us to search for the occurrence of a chitinase activity in human macrophages.

Indeed, as is documented below, we were able to demonstrate that, in contrast to previous believes, macrophages can produce a chitinase similar in properties to enzyme encountered in other non-mammalian organisms (17,18). The enzyme is highly capable of hydrolyzing chitin and also shows other common characteristics of chitinases. Based on the substrate initially used in the identification of the novel enzyme, i.e. 4-methylumbelliferyl-chitotrioside, the human chitinase has been named chitotriosidase (17).

A number of recent findings concerning chitotriosidase that were made at our laboratory are discussed. This information increases the insight in the features of this recently discovered enzyme.

Modest levels of chitotriosidase are detectable in lysosomes and specific granules of neutrophils. No chitotriosidase activity is demonstrable in erythrocytes, thrombocytes, lymphocytes and monocytes. We observed that exposure of neutrophils to lipopolysaccharide (LPS) results in release of chitotriosidase. In healthy volunteers administration of GM-CSF also leads to a temporary increase in plasma chitotriosidase levels, presumably caused by secretion of enzyme by neutrophils. The release of chitotriosidase mimicks that of lactoferrin. In isolated blood neutrophils no chitotriosidase mRNA was detectable. This suggests that the enzyme is produced in precursors of these cells in the bone marrow.

Chitotriosidase can be massively produced and secreted by macrophages. During the differentiation of cultured monocytes to macrophages production of chitotriosidase is a late event: only after one week of cell culture, the first mRNA and corresponding enzyme activity is detectable whilst other macrophage markers such as the tartrate resistant acid phosphatase are induced much earlier during the differentiation process. It appears that a particular kind of activation of macrophages, that spontaneously occurs during long-term culture of peripheral blood derived cells, is required for induction of chitotriosidase. Isolated peritoneal macrophages of the rat do not produce chitotriosidase, not even after prolonged culture. It is conceivable that some types of differentiated tissue macrophages are no longer able to synthesize chitotriosidase. Furthermore, not every trigger causing activation of macrophages may be compatible with chitotriosidase induction. We noted that activation of monocyte-derived macrophages with lipopolysaccharide (LPS) did in fact reduce secretion of chitotriosidase.

A potent trigger for chitotriosidase production by macrophages is apparently generated by lysosomal (glyco)lipid accumulation. It was noted that plasma chitotriosidase activities are elevated in a variety of lysosomal lipidoses, e.g. Niemann-Pick disease, Krabbe disease, GM1 gangliosidosis, and Wolmann Disease, although far less spectacular than in Gaucher disease. Interestingly, lysosomal storage disorders characterized by the accumulation of specific oligosaccharides or mucosaccharides are not accompanied by chitotriosidase elevations. It has become clear that the glucocerebrosidase deficiency in cells of Gaucher disease patients is in itself not causing excessive chitotriosidase production. Presymptomatic or asymptomatic Gaucher patients do not show abnormal chitotriosidase levels. Abnormal enzyme levels do correlate with clinical manifestation of Gaucher disease, i.e. the occurrence of lipidloaden macrophages in tissues and bone marrow.

It is currently felt that markedly elevated levels of chitotriosidase in plasma are a reflection of the presence of macrophages in a particular state of activation. Increased enzyme levels have been noted in patients with inherited lysosomal lipidoses, in patients with visceral Leishmaniasis, and patients with Sarcoidosis. It is of interest to note that the Leishmania parasite also resides in lysosomes of macrophages and possibly sheds glycolipid-like structures. The etiology of Sarcoidosis is so far not known. The disease, that might be due to an infectious agent such as mycobacterium, involves immunological granuloma formation containing multinucleate giant cells with features of macrophages.

Chitotriosidase may prove to be a useful marker for other disease states in which pathological macrophages are involved. One attractive candidate is formed by atherosclerosis, that is characterized by the presence of cholesterol-loaden macrophages. Moreover, we have noted elevated chitotriosidase levels in cerebral spine fluid of patients suffering from X-linked adrenoleukodystrophy and multiple sclerosis. It is believed that in both disorders activated brain macrophages (microglial cells) are an essential feature of the pathogenesis.

Clearly, chitotriosidase can be used as a diagnostic marker for onset of Gaucher disease, and most likely other lysosomal lipidoses. Furthermore, detection of elevated plasma enzyme levels may be useful in the diagnosis of Sarcoidosis and detection of elevated enzyme levels in cerebral spine fluid in the case of some neurodegenerative disorders. Moreover, the correction in enzyme levels upon therapeutic intervention may be an important tool to monitor the efficacy of treatment and could serve as a guideline for optimalization of therapy.

In order to use the human chitinase (chitotriosidase) as a (pharmaceutical) agent against chitin-containing organisms in vivo, a number of conditions have to be fulfilled.

An important issue is the tolerance of the body for chitotriosidase. As mentioned above, the human body is not believed to contain endogenous chitin. In analogy to lysozyme, a chitinase activity should therefore be harmless for the body. Since chitotriosidase is an endogenous protein that occurs in the circulation, it appears unlikely that an immune response is elicited by additional administration of the enzyme to man. Large concentrations of the chitotriosidase can be encountered in the circulation of patients with Gaucher disease, which is a recessively inherited lysosomal storage disorder characterized by the massive occurrence of glucosylceramide loaden macrophages in various tissues (17). The excessive amounts of the enzyme in plasma of Gaucher patients are without any apparent harmful consequences. This finding suggests that excessive amounts of chitotriosidase in the circulation are well tolerated by man, an important prerequisite for its potential use to combat chitin-containing pathogens.

In order to be useful as an agent against chitin-containing pathogens chitotriosidase has furthermore to be available in large quantities in a uniform state. There are no ubiquitous, natural sources for the isolation of the human chitinase. The mounts of enzyme in urine and placentas are low. This led us to attempt to isolate cDNA encoding chitotriosidase. Due to the specific expression of the chitotriosidase gene in macrophages, all tested cDNA libraries from other cell types were found to be negative for chitotriosidase cDNA. However, a constructed cDNA library from mRNA of long-term cultured macrophages that secreted massive amounts of chitotriosidase activity proved to be extremely rich in cDNAs encoding chitotriosidase, (0.1% of total cDNA). Two distinct cDNAs were in this manner identified and cloned.

The occurrence of two distinct cDNA species is due to alternative splicing of RNA, resulting in two distinct mRNA species which are both functional. Expression of the two cDNAs in COS cells results in synthesis and secretion of two discrete chitotriosidase proteins with apparent molecular weights of 39 and 50 kDa with polyacrylamide gel electrophoresis in the presence of sodium dodecyl sulphate. Both recombinant produced chitotriosidase isozymes, named chitozyme 50 and chitozyme 39, were enzymatically active. Further characterization of the recombinant chitotriosidase isozymes indicated that their specific activity, i.e. enzymatic activity per amount of antigen, was identical to that of chitotriosidase isolated from tissue or present in plasma.

As described in the section 'Experimental Data' in detail, the two chitotriosidase proteins are largely identical, being only distinct in their C-terminal portions. The isozymes contain the highly conserved, presumed catalytic center region of chitinases belonging to class 18 of glycosylhydrolases (19). The nucleotide sequences of the cloned cDNAs predict that both chitotriosidase proteins lack N-linked glycans. Indeed, the presence of any glycans was not demonstrable for the 39 kDa form. The presence of O-linked glycosylation cannot be excluded for the 50 kDa form.

The findings suggest that large scale recombinant production of both forms of human chitotriosidase using conventional techniques should be feasible. Moreover, it seems likely that not only production of the human enzyme in eukaryotic cells, but even in prokaryotes might be possible, since highly homologous proteins are endogenously produced by some of these organisms, e.g. Serratia marcescens. A procedure for the purification of chitotriosidase has been successfully developed (18; and below) It therefore will be possible to obtain large amounts of both recombinant human chitotriosidases in a pure and uniform state suitable for administration to man.

The 39 kDa chitozyme is not a glycosylated protein, so its production in prokaryotic cells should certainly be feasible. Bacteria which produce and secrete highly homologous chitinases should in principle be able to secrete correctly folded human chitotriosidase in their exoplasmic space, provided that a correct leader sequence is used. Alternatively, it could be considered to use yeast cells for the production of recombinant chitotriosidase, at least the 39 kDa chitozyme. It can so far not be excluded, however, that also 50 kDa chitotriosidase can be produced, not only in higher eukaryotes, but also in lower eukaryotes or even in prokaryotes.

Production of the chitozymes via conventional technology in insect cells, plant cells, or vertebrate cells should be possible. Finally, transgenic animals could be envisioned as producers of large quantities of chitozymes in their milk for the applications described above. It was observed that chitozyme when added to cow milk was completely stable for several hours at 37° C.

Another constraint in the application of an enzyme as therapeutic agent is formed by its ability to survive and to be functional in the body. Attention has therefore been focussed to the properties of chitotriosidase.

Both forms of recombinant chitotriosidase (chitozymes 39 and 50) prove to be extremely stable against a variety of proteases. Successful proteolytic cleavage is only accomplished after denaturation of the enzyme, e.g. after heating in the presence of sodium dodecylsulphate. Prolonged incubation of serum or plasma at 37° C. does not result in detectable loss of enzyme activity, suggesting that the enzyme is insensitive to serum proteases. In analogy, chitotriosidase is stable at 37° C. in macrophage-conditioned medium that contains large quantities of various other secreted lytic enzymes.

Further analysis revealed that the chitotriosidase isozymes are comparably stable and enzymatically active in the pH range of from 3 to 8. Moreover the enzyme is completely stable at 50° C. and enzyme activity is still recovered after spotting an enzyme solution on filter paper followed by storage for several days at room temperature. No loss of enzyme activity occurs upon storage at −20 or −70° C., and repeated cycles of freezing and thawing.

All these observations suggest that the chitotriosidase isozymes are truly stable enzymes, intrinsically highly resistant against denaturation and showing the potential to be functional in various environments.

A prerequisite for the intravenous application of the chitinase is insight in its clearance. In the blood stream the most predominant isozyme is the 50 kDa protein. In tissue predominantly a 39 kDa isozyme is encountered. This appears to be formed by uptake of 50 kDa protein followed by proteolytic cleavage to a 39 kDa form that is remarkably stable in the lysosomal environment. Experiments in rats suggest that the half life of recombinant 50 kDa chitotriosidase in the circulation is somewhat longer than that of the 39 kDa enzyme. Clearance is not a very rapid process as monitored by the disappearance of activity of human chitotriosidase in the blood stream of intravenously injected rats, the half life being about one hour. Only minor amounts of chitotriosidase are daily excreted into the urine. It is conceivable that some enzyme is efficiently recaptured by proximal tube epithelial cells since kidney is found to be extremely rich in 'lysosomally processed' 39 kDa enzyme. The observations so far suggest that intravenous administration can lead to a high level of human chitinase activity in the circulation for a prolonged period of time, allowing enzyme to reach various tissue locations.

Purified chitotriosidases are well able to hydrolyse chitin and artificial chitin-like substrates such as PNP-chitotrioside, PNP-chitobioside, 4MU-chitotrioside and 4MU-chitobioside. Moreover, it was noted that addition of chitotriosidase to a fungus (Mucor species) inhibited growth. These findings are in line with the expectations based on the high level of homology of chitotriosidase with chitinases from other species.

Summarizing, both chitotriosidase enzymes have properties that are advantageous with respect to their use as therapeutic agent. Both forms of the enzyme can be relatively easy produced via conventional recombinant techniques. The enzymes are extremely stable and capable of enzymatic activity under various conditions. The recombinant chitozyme 39 and chitozyme 50, and tissue chitotriosidase are not immediately cleared from the circulation, at least in the rat model, and could in principle be distributed to various tissue locations. The above findings concerning chitotriosidase have prompted us to claim here that natural and recombinant chitotriosidases (chitozymes) are attractive agents for use in intervention of infectious diseases due to organisms that contain chitin or related structures that are susceptible to hydrolysis by the enzyme.

The two recombinant chitotriosidases, chitozyme 50 and chitozyme 39, have so far always been found to be identical in enzymatic properties, i.e. specific activity, pH dependence and stability. Both chitozymes might be used as agents against various pathogens containing chitin (see Table 1). Infections with chitin-containing pathogens occur at various locations in the body. Due to their intrinsic properties chitozymes can be considered to be suitable for application at various body locations.

Topical application can be considered for the treatment of infections of superficial mycoses that occur at the skin.

Infections in the eye, reproductive tract and intestinal tract by chitin-containing organisms could also be treated by local administration. Relevant infections of the pulmonary system could be treated by use of a spray containing enzyme. Oral administration can be considered for the use against infectious chitin-containing organisms in the mouth and gastrointestinal tract. Finally, as indicated in the previous section, intravenous administration can be considered for intervening with pathogens present in the blood stream and tissues, either interor intra-cellularly. Additional research should reveal whether more specific targetting is possible by the use of specific chitozyme isoforms.

This invention furthermore embraces several variants and modifications, such as especially the following possibilities.

A. Use of a cocktail of recombinant human chitinase and β-1,3-glucanase

It is well documented that both in plants and fish chitinases play an important role in resistance against fungal infections. In plants, chitinases act synergistically with β-1,3glucanases since the cell walls of fungi are composed of a mixture of chitin and βglucan fibrils (15). At present it is believed that man is not capable of producing a chitinase nor a β-glucanase. However, it was noted that long-term cultured macrophages are not only able to secrete a chitinolytic enzyme but also an enzyme active against dye-labeled β-glucan. We therefore propose that analogous to the situation in plants a mixture of human chitinase and β-glucanase could be a more powerful anti-fungal agent than one of these enzymes alone. Isolation of the β-glucanase produced by long-term cultured macrophages and subsequent cloning of corresponding cDNA, should result in the availability of recombinant human β-glucanase for this purpose.

B. Use of modified recombinant human chitinase

Increasing insight in the 3-dimensional structure of chitotriosidase and the function of its several domains will allow engineering of modified forms of the enzyme for specific applications. For example, production of recombinant enzyme lacking domains that are not essential for catalytic activity and specificity might lead to a much smaller core protein that is still active and meanwhile more easily penetrates specific locations in the body. The currently available and rapidly extending knowledge about the structure of family 18 and family 19 glycosylhydrolases suggests that engineering of modified forms of chitinases is a realistic option.

In addition to therapeutical applications, the invention also embraces prophylactic applications.

We observed that plasma chitotriosidase activity tends to be higher with increasing age, being on the average severalfold higher in plasma of individuals older than 60 years of age than children. Moreover, we found that 1 in about every 15 individuals is unable to produce active chitotriosidase (see ref.17). These individuals are deficient in enzyme activity in plasma and urine, and in leukocytes and long-term cultured macrophages derived from peripheral blood monocytes. Chitotriosidase deficiency occurs with a similar frequency among patients with Gaucher disease as normal subjects. The clinical course of the disease is identical in patients that are deficient and those with several thousand-fold elevated plasma enzyme levels. This indicates that the chitotriosidase elevation is a hallmark of, but not a prerequisite for, clinical manifestation of Gaucher disease.

It was noted by us that chitotrisidase deficiency is an inherited trait. Strongly reduced levels of chitotriosidase mRNA as well as protein were observed for long-term cultured macro-phages obtained from peripheral blood monocytes of individuals deficient in chitotriosidase. The fact that the residual chitotriosidase protein shows a normal molecular mass and lacks enzymatic activity suggests that at least in these cases the underlying defect is some mutation in the chitotriosidase gene. Metabolic labeling and Northern blot analysis suggest that this mutation results in reduced synthesis of a catalytically impaired chitotriosidase protein.

It cannot be excluded that a deficiency in chitotriosidase may be associated with some disadvantage. For example, the resistance against chitin-containing pathogens could be reduced and lysosomal degradation of chitin in phagocytes could be impaired, resulting in abnormal behaviour of the cells. Further research is required to establish whether a chitotriosidase deficiency is indeed associated with some risks. If this proofs to be the case, prophylactic administration of human chitotriosidase to deficient individuals could be considered.

Other situations that may lead to a functional deficiency in chitotriosidase activity are immunodeficient states. We noted for example that in patients with acquired immuno-deficiency due to a HIV infection plasma chitotriosidase levels are on the average reduced. Furthermore it was noted that corticosteroid treatment of patients with Sarcoidosis resulted in a rapid reduction of chitotriosidase activity. Apparently the presence of activated macrophages is an important factor in maintaining normal chitotriosidase levels in the circulation. Supplementation with recombinant chitotriosidase may be considered in immuno-incompetent individuals that are at increased risk for infections with chitin-containing pathogens.

Local application of recombinant chitotriosidase could be also considered in the case of wounds to reduce the risk of infections with fungi.

The availability of a human chitinase could be also exploited as a tool to degrade injected or implanted chitin-based structures for medical purposes.

For example, drugs could be incorporated in chitin based capsules ('chitosomes'). The concomitant presence of well defined amounts of human chitinase in the capsule could ensure a controlled release of drugs. A slow but gradual release of drug could particularly be envisioned when it is trapped in a chitin matrix. The use of the human enzyme in such a system would result in ultimate destruction of the chitin-based capsule and not elicit an immunological response. The drugs used in such a system could vary from small compounds to proteins and DNA fragments for the purpose of enzyme and gene therapy. Chitin (or analogues) is already employed as a carrier for drugs (20).

Another, related, application is the use of recombinant chitotriosidase for the swift degradation of implants that contain chitin as a structural component. This would be useful in the case of implants that only temporarily have to fulfil a function and can be conveniently 'dissolved' by administration of recombinant chitotriosidase.

Recombinant chitotriosidase can be also used ex vivo as a fungicidal compound. For example, as a preventive measure recombinant chitotriosidase (or a cocktail with β-1,3-glucanase) could be added to culture medium of human cells that preferably need to be cultured in the absence of antibiotics and have to be re-administered to the human body. Examples in this connection may be the ex vivo culture of cells for the purpose of gene therapy and the ex vivo culture of keratinocytes to be used in connection with wound healing.

Finally, recombinant human chitotriosidase (or a cocktail with β-1,3-glucanase) may be used as an additive in tooth paste and body lotions in order to prevent fungal infections.

The invention will now be illustrated by the following examples which merely serve to exemplify the invention and are not intended to limit the scope of the invention.

EXAMPLE 1

Cloning and Composition of cDNAs Encoding Human Chitotriosidases

In order to clone cDNA encoding human chitotriosidase the following strategy was used. Chitotriosidase was purified from spleen of a type 1 Gaucher disease patient since this organ is extremely rich in chitotriosidase activity (18). The N-terminal amino acid sequence of chitotriosidase was determined and this information was used for cloning chitotriosidase cDNA. Firstly, the established N-terminal amino acid sequence of chitotriosidase (18) was used to design a degenerate sense oligonucleotide: 5'-TGYTAYTTYACNAAYTGGGC-3'(SEQ ID NO:1). Secondly, a degenerate anti-sense nucleotide was designed based on the highly conserved domain among chitinases that is presumed to be an essential part of the catalytic center: 5'-CCARTCIARRTYIACICCRTCRAA-3' (SEQ ID NO:2).

These oligonucleotides were used to amplify a DNA fragment by RT-PCR. For this purpose, total RNA had been isolated from long-term cultured macrophages that secreted large amounts of chitotriosidase activity. First strand cDNA synthesis was performed using SuperScript TM RNAse H, reverse transcriptase and oligo dT. After alkaline hydrolysis, the cDNA was precipitated with ethanol and used as template. PCR was performed using standard conditions. The DNA fragment obtained by RT-PCR was of the expected size (on the basis of homology with members of the chitinase family). The fragment was purified, treated with T4 DNA polymerase and cloned into the HindII site of the plasmid vector pUC19. Determination of its sequence using the dideoxy-nucleotide chain termination method revealed that the fragment was in complete accordance with the known N-terminal amino acid sequence of purified human chitotriosidase, allowing its use as a probe to identify a full length chitotriosidase cDNA.

A cDNA library was prepared using total RNA from cultured macrophages. Double stranded macrophage cDNA was prepared from RNA using the SuperScript Choice System cDNA Synthesis Kit from GIBCO-BRL. Double stranded cDNA was ligated to an excess of non-palindromic BstX1 linkers and subsequently size fractionated on a low melting type agarose gel. The cDNA exceeding 500 bp was purified and ligated into BstX1 sites of the vector pcDNAl (InVitrogen). The ligation mixture was electroporated into Escherichia coli strain MC106/p3 to obtain a macrophage cDNA library.

The cDNA library was screened by colony hybridization using the partial chitotriosidase cDNA probe that had been radiolabelled by the random priming method. Hybridization to the probe was carried out for 4 h in 1 mM EDTA, 0.5 M sodium hydrogen phosphate buffer (pH 7.2) containing 7% (w/v) sodium dodecylsulphate at 65° C. Next, the filters were washed twice in 150 mM sodium chloride, 15 mM sodium citrate (pH 7.0) containing 0.1% (w/v) sodium dodecylsulphate, and subjected to autoradiography. About 0.1% of the colonies were positive upon hybridization with the partial chitotriosidase cDNA clone. About 20 clones were sequenced as described above. Two distinct, full length chitotriosidase cDNAs were in this manner identified. The two clones are designated as chi.50 and chi.39.

The nucleotide sequence (SEQ ID NO:3) of the cDNA clone chi.50 shows an open reading frame starting with an ATG at position 13 and ending with a TGA codon at position 1410 (see FIG.1). The open reading frame encodes a protein with a characteristic N-terminal ER signal peptide, immediately followed by the N-terminal sequence established for the chitotriosidase protein. The cDNA sequence does not indicate the presence of potential N-linked glycosylation sites, which is consistent with the absence of N-linked glycans in isolated chitotriosidase. The predicted protein, after removal of the signal sequence, has a length of 445 amino acids and a calculated molecular mass of 49 kDa. Metabolic labelling experiments with cultured macrophages revealed that these cells predominantly synthesize and secrete a chitotriosidase protein with apparent molecular mass of 50 kDa with polyacrylamide gel electrophoresis in the presence of sodium dodecylsulphate at reducing conditions. The predicted C-terminal part of 50 kDa human chitotriosidase is rich in serine residues of which theoretically some might be O-linked glycosylated. The occurrence of this type of glycans in 50 kDa human chitotriosidase has so far not been excluded or confirmed.

The nucleotide sequence (SEQ ID NO:5) of the cDNA clone chi.39 shows an open reading frame that encodes an almost identical chitotriosidase protein with a total of 387 amino acids (see FIG. 2). After removal of the hydrophobic leader, the predicted protein for chi.39 cDNA has a length of 366 amino acids and expected molecular mass of 39 kDa. The signal peptide and the first 384 amino acids are identical to those in the chitotriosidase protein encoded by the chi.50 cDNA. Only the 3 most C-terminal amino acids in the predicted 39 kDa chitotriosidase are distinct from those in the protein predicted for chi.50 cDNA.

Comparison of the nucleotide sequences of both cDNAs suggests that an additional sequence of nucleotides is inserted in the chi.39 cDNA.

Again, no N-linked glycosylation is predicted for the chi.39 cDNA encoded chitotriosidase.

The relationship between various forms of chitotriosidase is shown in FIG. 3.

The composition of the two cloned chitotriosidase cDNAs strongly suggested that alternative splicing causes the formation of two distinct mRNAs. The chi.39 cDNA contains an additional exon of the chitotriosidase gene as compared to the chi.50 cDNA, as was experimentally verified. Genomic chitotriosidase DNA was cloned and partially sequenced. The sequence shows indeed intron-exon transitions that are consistent with the assumption that the two distinct cDNA clones (representing different mRNA species) are the result of alternative splicing of chitotriosidase RNA.

Metabolic labelling experiments with cultured macrophages showed that concomitantly large amounts of 50 kDa chitotriosidase protein and very small amounts of a 39 kDa protein were initially synthesized. In accordance with these findings, RNAse protection analysis revealed the concomitant presence of chi.50 RNA and minor amounts of chi.39 RNA in macrophages. It was furthermore noted that secreted 50 kDa chitotriosidase can be proteolytically processed to a 38–39 kDa protein after uptake by macrophages. It may be that some newly synthesized chitotriosidase is not secreted, but directly routed to the lysosomal apparatus where it is further proteolytically processed.

From spleen of Gaucher disease patients at least two isoforms of chitotriosidase can be isolated. The apparent molecular masses are 50 and 39 kDa with polyacrylamide gel electrophoresis in the presence of sodium dodecylsulphate. The exact molecular mass for 39 kDa chitotriosidase isolated from tissue was determined using electron spray mass spectrometry. This analysis indicates that the 39 kDa tissue enzyme (that has the normal N-terminus) has undergone C-terminal proteolytic processing. It should be noted that proteolytic processing of the 39 kDa precursor (removal of four C-terminal amino acids) as well as the 50 kDa precursor (removal of 83 C-terminal amino acids) would both yield the tissue enzyme.

A search of the EMBL and GenBank databases revealed significant homology between the two human chitotriosidases and a group of chitinases and related proteins from different species. All the homologous proteins belong to the so called 'chitinase protein family' (18,19).

The strongest homology is noted for a region that is presumed to be an essential element of the catalytic center in chitinases (see FIG. 4). Additional homologous regions with members of the chitinase family were identified. In FIG. 1 the amino acids in 39 kDa chitotriosidase that are identical to those in at least 6 out of 9 members of the chitinase protein family are indicated by bold characters.

The predicted C-terminal part of 50 kDa human chitotriosidase shows only homology with two chitinases from Manduca sexta and Brugia malayi, respectively. In the case of the latter enzyme O-linked glycosylation has been reported (12).

EXAMPLE 2

Recombinant Production of Human Chitotriosidases

COS-1 cells were transiently transfected with the two chitotriosidase cDNAs by the DEAE-Dextran method as described previously (21). The production of chitotriosidase was monitored by measurement of secreted enzyme activity. The chitotriosidase activity in culture medium was measured using the fluorogenic substrate 4-methylumbelliferyl-chitotrioside as described before.

The medium of COS cells, transfected with either chi.50 or chi.39 cDNA, contained 7 days after transfection large amounts of chitotriosidase activity (5–20 mU/ml). No activity was detected in the case of mock transfected COS cells or cells transfected with the same cDNA inserted in the anti-sense orientation.

Figure 5:
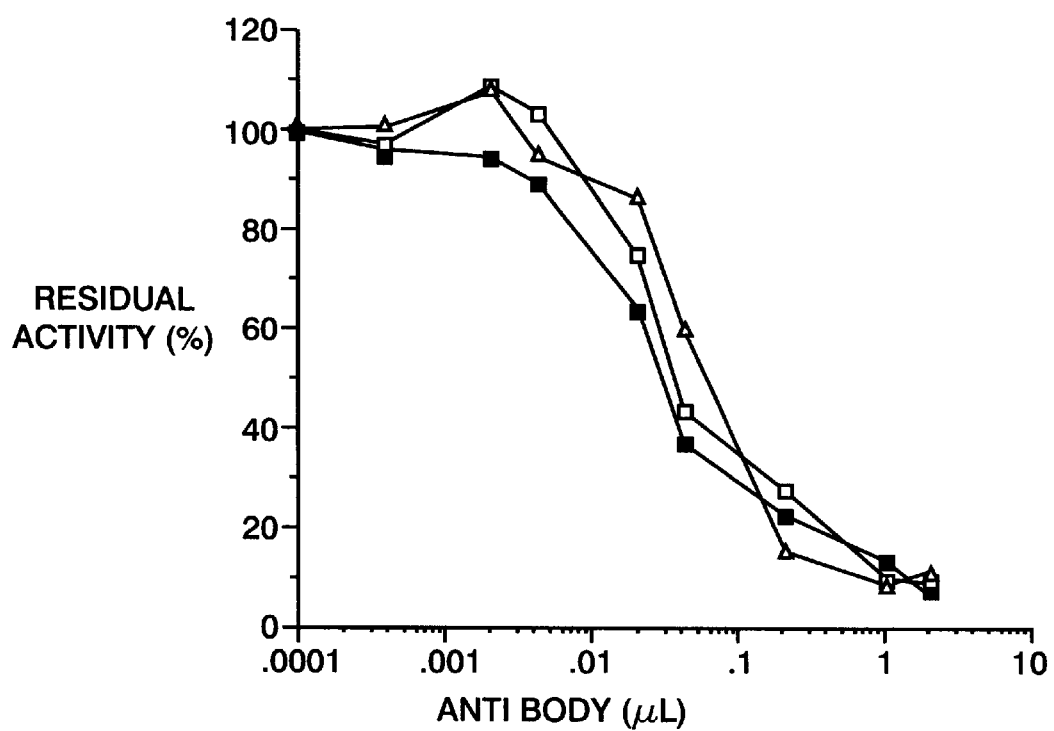
FIG. 5. Immunotitration of 39 and 50 kDa chitotriosidase purified from spleen and that of 39 and 50 kDa enzyme produced by transfected COS cells.

The chitotriosidase produced by COS cells was analysed by immunotitration with a rabbit antiserum against human chitotriosidase. This antiserum is capable of inhibiting human chitotriosidase in its enzymatic activity. FIG. 5 shows that chitotriosidase is inactivated by the antiserum in an identical manner to isolated splenic chitotriosidase. This finding suggests that the enzymatic activity per amount of antigen is similar in the case of the two recombinant chitotriosidases and the splenic enzyme.

No differences were noted in pH-profile, stability, Km for 4-methylumbelliferyl-chitotrioside and 4-methylumbelliferyl-chitobioside when both recombinant enzymes ('50 and 39 chitozymes') were compared with splenic chitotriosidase.

Metabolic labelling experiments revealed that the COS cells transfected with the chi.50 cDNA and chi.39 cDNA, respectively, produced chitotriosidase proteins with the expected molecular masses of 50 and 39 kDa, respectively.

EXAMPLE 3

Purification of Chitotriosidases

Previously we developed a procedure for the purification of 39 kDa and 50 kDa chitotriosidase from Gaucher disease spleen (18). The procedure renders pure 39 kDa chitotriosidase and partially pure 50 kDa enzyme.

Briefly, a detergent-free extract is applied to a polybuffer exchange column (PBE 94, Pharmacia Biotech Inc.); the column is equilibrated and eluted with 25 mM Tris buffer (pH 8.5). Breakthrough fractions with highest chitotriosidase activity are pooled and concentrated by ultrafiltration. This pool is applied to a Sephadex C-1000 column and eluted with 25 mM Tris buffer (pH 8.0). Peak fractions containing enzyme activity are pooled, concentrated and subjected to preparative isoelectric focussing using Ultrodex (Pharmacia) containing 0.5% (v/v) Triton X-100 and 0.1% (w/v) ampholytes (Servalyte 4–9, Serva). After focussing overnight at 10° C. and 400 V, the gel is fractionated and extracted with water. Fractions with pI 8.0 contain pure chitotriosidase with apparent molecular mass of 39 kDa with polyacrylamide gel electrophoresis in the presence of sodium dodecylsulphate. Fractions with pI around 7.2 contain 50 kDa chitotriosidase contaminated with some other proteins.

Complete purification of the impure 50 kDa chitotriosidase can be accomplished by incubation of enzyme preparation with chitin particles in citrate/phosphate buffer (pH 5.2) at 4° C., followed by elution at room temperature in the presence of 4 M sodium chloride in the same buffer. The contaminants are not bound or completely removed by washing of the chitin particles with ice-cold citrate buffer containing 0.1 M sodium chloride and 0.5% (v/v) Triton X-100.

The same isolation procedure is applicable for isolation of recombinant chitotriosidases (chitozymes) from culture medium cells transfected with chitotriosidase cDNAs.

The specific activity of purified 39 and 50 kDa recombinant chitotriosidase is identical to purified tissue enzyme, i.e. from 6 to 6.5 mmol substrate hydrolysis/mg protein x hour using the artificial substrate 4-methylumbelliferyl-chitotrioside at conditions previously described.

EXAMPLE 4

Degradation of Chitin

Purified 50 kDa and 39 kDa tissue chitotriosidases, and 50 kDa and 39 kDa chitozymes produced by recombinant DNA technology, are able to hydrolyse 4-methylumbelliferyl-chitotrioside and 4-methylumbelliferyl-chitobioside, the ratio of chitobioside activity to chitotrioside activity being about 0.7. Furthermore, p-nitrophenyl-chitotrioside and p-nitrophenyl-chitobioside are also efficiently hydrolyzed.

Chitin azure (Sigma) suspended in citrate/phosphate buffer (pH 5.2) at a final concentration of 10 mg/ml was used to monitor chitinase activity. Chitin degradation was detected spectrophotometrically at 550 nm by determination of release of soluble azure (18). Chitinase from Serratia marcescens (Sigma) was used as control. When related to the hydrolysis of 4-methylumbelliferyl-chitotrioside, the chitinase activity of human chitotriosidase was comparable to that of the bacterial chitinase. See for example ref.18.

No significant activity of human chitotriosidase towards a cell wall suspension of Micrococcus lysodeikticus was detectable, suggesting that the enzymes lack lysozyme activity.

EXAMPLE 5

Fungicidal Effect

To test whether human chitotriosidase can exert an antifungal action, a chitinous fungus (Mucor mucedo) was grown on plates (containing malt extract, peptone, glucose and agar) under a Cellophane membrane in order to keep the hyphae flat against the agar surface (see ref.16). Individual sectors were cut out and mounted on microscope slides. Purified chitozyme 50 and chitozyme 39 were dialysed against 0.15 M sodium chloride. Samples of enzyme-containing solutions, and 0.15 M NaCl were pipetted on the hyphal tips. Microscopical analysis revealed that application of enzyme resulted in immediate cessation of hyphal growth, followed by a distorted morphological appearance. Application of saline had no effect. Negative effects on hyphal growth were detectable using chitozyme solutions with a concentration of enzyme as little as 0.005 mg/ml.

LEGENDS TO THE DRAWINGS

FIG. 1. Nucleotide sequence (SEQ ID NO:3) of chi.50 cDNA clone and predicted amino acid sequence (SEQ ID NO:4) of corresponding protein.

The hydrophobic leader (amino acids 1–21) is underlined. Amino acids in chitotriosidase that are identical to those in at least 6 out of 9 members of the chitinase family are depicted in bold characters. The 9 members of the chitinase family used are listed in the legend of FIG. 4, with the exception of the chitinases from Autographa californica and Nicotiana tabacum.

FIG. 2. Nucleotide sequence (SEQ ID NO:5) of chi.39 cDNA clone and predicted amino acid sequence (SEQ ID NO:6) of corresponding protein.

The hydrophobic leader (amino acids 1–21) is underlined.

FIG. 3. Schematic overview of various chitotriosidase isozymes produced in macrophages.

Due to alternative splicing, two distinct mRNAs are generated that are translated into chitotriosidase proteins with apparent molecular masses of 39 and 50 kDa. Both forms are predominantly secreted. However, some enzyme may be directly routed to lysosomes or be endocytosed and reach this compartment. In the lysosome, further proteolytic processing of the C-terminus may occur to a form of about 38–39 *kDa. Both precursors (*39 and 50 kDa) can in this way be processed to an identical lysosomal form. It cannot be excluded that the C-terminal part of 50 kDa chitotriosidase contains O-linked glycans. The 39 kDa precursor and the lysosomally processed chitotriosidase are free of glycans.

FIG. 4. Alignment of putative active site regions in some members of the chitinase protein family.

The proteins are: human chitotriosidase (SEQ ID NO:7); a chitinase from the virus Autographa californica (GenBank L22858(SEQ ID NO:8)); a chitinase from the tobacco hornworm Manduca sexta (GenBank U02270(SEQ ID NO:7)); an endochitinase from the nematode Brugia malayi (Genbank M73689(SEQ ID NO:9)); a human oviductal glycoprotein (GenBank U09550(SEQ ID NO:10)); HCgp-39, a human glycoprotein produced by chondrocytes and synovial cells (GenBank M80927(SEQ ID NO:11)); YM-1, a secretory protein of activated mouse macrophages (Pir S27879(SEQ ID NO:12)); a chitinase from the fungus Aphanocladium album (SwissProt P32470(SEQ ID NO:13)); a chitinase from the filamentous fungus Trichoderma harzianum (GenBank L14614(SEQ ID NO:14)); chitinase A1 from the prokaryote Bacillus circulans (SwissProt P20533(SEQ ID NO:15)); and a class V chitinase from the plant Nicotiana tabacum (GenBank X77110(SEQ ID NO:16)). Residues identical to chitotriosidase are indicated by the inverted characters. The proteins HCgp-39 and YM-1 are supposed to be not chitinolytic.

FIG. 5. Immunotitration of 39 and 50 kDa chitotriosidase purified from spleen and that of 39 and 50 kDa enzyme produced by transfected COS cells.

Preparations containing either purified 39 kDa splenic chitotriosidase ( ), or 50 kDa chitozyme produced by COS cells transfected with chi.50 cDNA ( ), or 39 kDa chitozyme produced by COS cells transfected with chi.39 cDNA were incubated for 1 hour at room temperature in phosphate buffered saline with different amounts of rabbit (anti-human splenic chitotriosidase) antiserum.

Binding of antibody to chitotriosidase results in loss of enzymatic activity. Residual enzyme activity upon incubation of enzyme preparations with antiserum was determined by measurement of activity towards the substrate 4-methylumbelliferyl-chitotrioside (18). The similarity in the immunotitration curves of various chitotriosidases indicates that the enzymes are identical in enzymatic activity per amount of antigen.

REFERENCES

1. Immunology (3rd ed; eds Roitt, I., Brostoff, J., Male, D.) (1993), Mosby, London.
2. Cohen, E. (1993), Arch. Insect. Biochem. Physiol. 22, 245–261. Chitin synthesis and degradation as targets for pesticide action.
3. Mulisch, M. (1993), Eur. J. Protistol. 29, 1–18. Chitin in protistan organisms. Distribution, synthesis and deposition.
4. Bulawa, C. E. (1993), Annu. Rev. Microbiol. 47, 505–534. Genetics and molecular biology of chitin synthesis in fungi.
5. Flach, J., Pilet, P.-E., Jolles, P. (1992), Experienta 48, 701–716. What is new in chitinase research ?
6. Henrissat, B. (1991), Biochem. J. 280, 309–316. Classification of glycosylhydrolases based on amino acid sequence similarities.
7. Coulson, A. F. W. (1994), FEBS Letters 354, 41–44. A proposed structure for 'family 18' chitinases. A possible function for narbonin.
8. Perrakis, A., Tews, I., Dauter, Z., Oppenhem, A. B., Chet, I., Wilson, K. S., Vorgias, C. E. (1994), Structure 2, 1169–1189. Crystal structure of a bacterial chitinase at 2.3 angstrom resolution.
9. Wansborough-Jones, M. N., Wright, S. G., McManus, T. J., Infectious, Tropical and Parasitic Diseases (Chapter 12) in: Textbook of Medicine (Souhami,R. L., Moxham, J.,eds) (1990), Churchill Livingstone, London
10. Shahabuddin, M., Kaslow, D. C. (1994), Exp. Parasitol. 79, 85–88. Plasmodium: parasite chitinase and its role in malaria transmission.
11. Nussenzweig, R. S., Long, C. A. (1994), Science 265, 1381–1383. Malaria Vaccines: Multiple targets.
12. Fuhrman, J. A., Lane, W. S., Smith, R. F., Piessens, W. F., Perler, F. B. (1992), Proc. Natl. Acad. Sci. USA 89, 1548–1552. Transmission-blocking antibodies recognize microfilarial chitinase in brugian lymphatic filariasis.
13. Raghavan, N., Freedman, D. O., Fitzgerald, P. C., Unnasch, T. R., Ottesen, E. A., Nutman, T. B. (1994), Infection and Immunity 62, 1901–1908. Cloning and characterization of a potentially protective chitinase-like recombinant antigen from Wucheria bancrofti.
14. Sahai, A. S., Manochoa, M. S. (1993), FEMS Microbiology Reviews 11, 317–338. Chitinases of fungi and plants: their involvement in morphogenesis and host-parasite interaction.
15. Shapira, R., Ordentlich, A., Chet, I., Oppenheim, A. B. (1989), Phytopathology 79, 1246–1249. Control of plant diseases by chitinase expressed from cloned DNA in Escherichia coli.
16. Manson, F. D. C., Fletcher, T. C., Gooday, G. W. (1992), J. Fish Biology 40, 919–927. Localization of chitinolytic enzymes in blood of turbot, Scophtahalmus maximus, and their possible roles in defence.
17. Hollak, C. E. M., van Weely, S., van Oers, M. H. J., Aerts, J. M. F. G. (1994), J. Clin. Invest. 93, 1288–1292. Marked elevation of plasma chitotriosidase activity. A novel hallmark of Gaucher disease.
18. Renkema, G. H., Boot, R. G., Muijsers, A. O., Donker-Koopman, W. E., Aerts, J. M. F. G. (1995), J. Biol. Chem. 270, 2198–2202. Purification and characterization of human chitotriosidase, a novel member of the chitinase family of proteins.
19. Hakala, B. E., White, C., Reclies, A. D. (1993), J. Biol. Chem. 268, 25083–25810. Human cartillage gp-39, a major secretory product of articular chondrocytes and synovial cells, is a mammalian member of the chitinase protein family.
20. Miyazaki, S., Ishii, K., Nadai, T. (1981), Chem. Pharm. Bulletin 29, 3067–3069. The use of chitin and chitosan as drug carrier.
21. Lopata, M. A., Cleveland, D. W., Sollner-Webb, B. (1984), Nucleic Acid Res. 12, 5701–5707.

What is claimed is:

1. A method of therapeutic or prophylactic treatment of a human individual against infection by a chitin-containing pathogen, comprising administering to said human individual a pharmaceutical composition comprising a substantially isolated or purified chitinase and a pharmaceutically acceptable carrier or diluent, said chitinase being a human chitinase having the amino acid sequence of SEQ. ID NO:4 or SEQ. ID NO:6 or a human chitinase having chitinase activity, which is encoded by a nucleic acid which hybridizes to SEQ. ID NO:3 or SEQ. ID NO:5 at 65° C., in 1 mM EDTA, 0.5 M sodium hydrogen phosphate (pH 7.2) containing 7% (w/v) SDS.

2. A method as described in claim 1,
   wherein said chitinase is produced by a genetically engineered host cell and isolated from said host cell or medium in which said host cell is cultured, and
   wherein the amino acid sequence of the chitinase is encoded by a nucleotide sequence selected from the group consisting of a nucleotide sequence depicted in SEQ ID NOS: 3 and 5.

3. A method as described in claim 1,
   wherein said amino acid sequence is an amino acid sequence depicted in SEQ ID NO:4.

4. A method as described in claim 1,
   wherein said amino acid sequence is an amino acid sequence depicted in SEQ ID NO:6.

5. A method as described in claim 1, wherein said pharmaceutical composition comprises a therapeutically or prophylactically effective amount of said chitinase.

6. A method as described in claim 5, wherein said pharmaceutical composition further comprises a therapeutically or prophylactically effective amount of a β-glucanase.

* * * * *

UNITED STATES PATENT AND TRADEMARK OFFICE
CERTIFICATE OF CORRECTION

PATENT NO.   : 6,303,118 B1
DATED        : January 10, 2002
INVENTOR(S)  : J.M.F.G. Aerts Page 1 of 1

It is certified that error appears in the above-identified patent and that said Letters Patent is hereby corrected as shown below:

<u>Title page,</u>
*Attorney, Agent, or Firm*, now reads "Hoffman & Baron, LLP"; this should read
-- Hoffmann & Baron, LLP --.

<u>Column 7,</u>
Line 23, now reads "...purified chitinase fom turbot..." should read
-- ...purified chitinase from turbot... --;

<u>Column 10,</u>
Line 48, now reads "...sequence of corresponding protein..." should read
-- sequence of corresponding protein (SEQ ID NO:6). --

<u>Column 13,</u>
Line 30, now reads "... and below) It therefore..." should read
-- ...and below). It therefore... --

Signed and Sealed this

Twenty-eighth Day of May, 2002

Attest:

*Attesting Officer*

JAMES E. ROGAN
*Director of the United States Patent and Trademark Office*